(12) United States Patent
Bavetta et al.

(10) Patent No.: US 9,241,517 B2
(45) Date of Patent: Jan. 26, 2016

(54) EAR PROTECTION DEVICE

(75) Inventors: Dean Bavetta, Philadelphia, MS (US); Paul Kay, Libertyville, IL (US); Brian E. Le Gette, Baltimore, MD (US); Gary F. Prokop, Wheaton, IL (US); Steve Remy, Chicago, IL (US)

(73) Assignee: 180s, Inc., Baltimore, MD (US)

( * ) Notice: Subject to any disclaimer, the term of this patent is extended or adjusted under 35 U.S.C. 154(b) by 0 days.

(21) Appl. No.: 13/277,196

(22) Filed: Oct. 19, 2011

(65) Prior Publication Data

US 2012/0131732 A1 May 31, 2012

Related U.S. Application Data

(63) Continuation of application No. 11/742,181, filed on Apr. 30, 2007, now abandoned, which is a continuation of application No. 11/108,614, filed on Apr. 18, 2005, now Pat. No. 7,210,173, which is a (Continued)

(51) Int. Cl.
*A41D 13/05* (2006.01)
*A61F 11/14* (2006.01)

(Continued)

(52) U.S. Cl.
CPC ............. *A41D 13/05* (2013.01); *A61F 11/14* (2013.01); *H04R 1/10* (2013.01); *H04R 5/0335* (2013.01); *A42B 3/16* (2013.01); *H04R 1/1066* (2013.01);

(Continued)

(58) Field of Classification Search
CPC .......... A61F 11/14; A61F 11/08; H42B 1/201

USPC ....... 2/209, 423, DIG. 11, 183; 381/370, 378, 381/379, 385, 371, 381; 181/129, 133, 137
See application file for complete search history.

(56) References Cited

U.S. PATENT DOCUMENTS

| 138,894 A | 5/1873 | Isidor |
| 139,831 A | 6/1873 | Stone |

(Continued)

FOREIGN PATENT DOCUMENTS

| CA | 2180036 | 1/1997 |
| CH | 294003 | 1/1954 |

(Continued)

OTHER PUBLICATIONS

Advertisement: The "PODZ" ear warming eye glass retainer, Shred Alert Products of Hood River, Oregon, 5 pgs.

(Continued)

*Primary Examiner* — Richale Quinn
(74) *Attorney, Agent, or Firm* — Cooley

(57) ABSTRACT

An apparatus comprising a first curved band portion and a second curved band portion. The first curved band portion has a first end, a second end, an inner curved side and an outer curved side. The first curved band portion defines a passageway between the first end and the second end of the first curved band portion. The passageway has a first opening. The second curved band portion has a first end, a second end, an inner curved side and an outer curved side. A motion-restraint portion is proximate to the first end of the second curved band portion. The first end of the second curved band portion is insertable into the first opening of the passageway of the first curved band portion. The first curved band portion has a range of motion within the passageway of the second curved band portion.

20 Claims, 17 Drawing Sheets

Related U.S. Application Data continuation of application No. 10/330,213, filed on Dec. 30, 2002, now Pat. No. 6,880,174, which is a continuation of application No. 10/024,523, filed on Dec. 21, 2001, now Pat. No. 6,499,146.

(60) Provisional application No. 60/259,114, filed on Dec. 29, 2000.

(51) Int. Cl.
  *H04R 1/10* (2006.01)
  *H04R 5/033* (2006.01)
  *A42B 3/16* (2006.01)

(52) U.S. Cl.
  CPC . *Y10S 2/11* (2013.01); *Y10T 24/314* (2015.01); *Y10T 24/34* (2015.01)

(56) References Cited

U.S. PATENT DOCUMENTS

| | | | |
|---|---|---|---|
| 145,168 | A | 12/1873 | Goge |
| 170,942 | A | 12/1875 | Edgar |
| 183,359 | A | 10/1876 | Abbott |
| 184,006 | A | 11/1876 | Edgar |
| 185,506 | A | 12/1876 | Edgar |
| 188,292 | A | 3/1877 | Greenwood |
| 190,720 | A | 5/1877 | Kleinert |
| 227,364 | A | 5/1880 | Kleinert |
| 315,233 | A | 4/1885 | Britton |
| 352,798 | A | 11/1886 | Barnes |
| 358,718 | A | 3/1887 | Basch |
| 359,425 | A | 3/1887 | Britton |
| 359,612 | A | 3/1887 | Kleinert |
| 360,985 | A | 4/1887 | Basch |
| 365,061 | A | 6/1887 | Friedman |
| 375,594 | A | 12/1887 | Basch |
| 381,559 | A | 4/1888 | Kleinert et al. |
| 389,735 | A | 9/1888 | Britton |
| 486,725 | A | 11/1892 | Mellor |
| 503,703 | A | 8/1893 | Kleinert |
| 516,135 | A | 3/1894 | Thamm |
| 529,176 | A | 11/1894 | Kleinert |
| 548,738 | A * | 10/1895 | Ballard .............. 2/208 |
| 758,680 | A | 5/1904 | Otte |
| 804,731 | A | 11/1905 | Keller |
| 836,087 | A | 11/1906 | Callahan |
| 869,741 | A | 10/1907 | Seitzman |
| 932,487 | A | 8/1909 | Melio |
| 953,623 | A | 3/1910 | Keller |
| 1,149,806 | A | 8/1915 | Basch |
| 1,167,368 | A | 1/1916 | Adams-Randall |
| 1,179,473 | A | 4/1916 | Taylor |
| 1,274,842 | A * | 8/1918 | Basch .............. 2/208 |
| 1,326,875 | A | 12/1919 | Miller |
| 1,395,864 | A | 11/1921 | Pape |
| 1,398,958 | A * | 12/1921 | Basch .............. 2/209 |
| 1,438,171 | A | 12/1922 | Delson |
| 1,567,105 | A | 12/1925 | Bohlman |
| 1,577,183 | A | 3/1926 | Dowiarz |
| 1,628,483 | A | 5/1927 | Wiegand et al. |
| 1,873,864 | A | 8/1932 | Ely |
| 1,945,110 | A | 1/1934 | Gordon |
| 1,988,880 | A | 1/1935 | Strouse |
| 2,070,216 | A | 2/1937 | Rosenberg |
| 2,120,189 | A | 6/1938 | Reinemer |
| 2,149,383 | A | 3/1939 | Bean |
| 2,184,996 | A | 12/1939 | Jacobs |
| 2,216,954 | A * | 10/1940 | McDonough ............ 2/209 |
| 2,241,736 | A | 5/1941 | Reinemer |
| 2,246,031 | A | 6/1941 | Baritz et al. |
| 2,314,782 | A * | 3/1943 | Goretsky ............ 2/209 |
| 2,333,392 | A | 11/1943 | Rosenzweig |
| 2,378,398 | A | 6/1945 | Fiedler |
| 2,405,326 | A * | 8/1946 | Plotsky ............ 2/209 |
| 2,420,245 | A * | 5/1947 | Hurst ............ 2/209 |
| 2,437,049 | A | 3/1948 | Salisbury et al. |
| 2,439,289 | A | 4/1948 | Fanslow |
| 2,447,078 | A | 8/1948 | Maxant |
| 2,464,331 | A | 3/1949 | Mason |
| 2,532,852 | A | 12/1950 | Oaks |
| 2,572,746 | A | 10/1951 | Mougel |
| 2,582,907 | A | 1/1952 | Kaufmann |
| 2,586,644 | A | 2/1952 | Gilbert |
| 2,609,544 | A | 9/1952 | Berg |
| 2,615,169 | A | 10/1952 | Maxant |
| 2,651,046 | A | 9/1953 | Berg |
| 2,671,221 | A * | 3/1954 | Triplett ............ 2/208 |
| 2,678,999 | A | 5/1954 | Norris |
| 2,693,599 | A | 11/1954 | Berg |
| 2,717,930 | A | 9/1955 | Hintz |
| 2,738,514 | A | 3/1956 | Gondell |
| 2,763,869 | A | 9/1956 | Bogart et al. |
| 2,776,436 | A | 1/1957 | Berg |
| 2,782,423 | A | 2/1957 | Simon et al. |
| 2,858,544 | A | 11/1958 | Roth |
| 2,899,683 | A | 8/1959 | Wadsworth et al. |
| 2,946,860 | A | 7/1960 | Jansen et al. |
| 3,087,028 | A | 4/1963 | Bonnin |
| 3,104,398 | A | 9/1963 | Palmaer |
| 3,112,493 | A * | 12/1963 | Greenberg ............ 2/209 |
| 3,119,119 | A | 1/1964 | Millinger et al. |
| 3,119,904 | A | 1/1964 | Anson |
| 3,156,923 | A | 11/1964 | Timm |
| 3,235,882 | A | 2/1966 | Coleman |
| 3,249,949 | A * | 5/1966 | Rosenberg et al. ............ 2/209 |
| 3,308,480 | A | 3/1967 | Elder |
| 3,311,713 | A | 3/1967 | Knuebel |
| 3,440,663 | A | 4/1969 | Beguin |
| 3,447,160 | A | 6/1969 | Teder |
| 3,505,684 | A | 4/1970 | Hutchinson et al. |
| 3,509,580 | A | 5/1970 | Rubenstein et al. |
| 3,686,691 | A | 8/1972 | Anderson |
| 3,721,993 | A | 3/1973 | Lonnstedt |
| 3,728,741 | A | 4/1973 | Lepor |
| 3,787,899 | A | 1/1974 | Krawagna |
| 3,815,155 | A | 6/1974 | Davison et al. |
| 3,841,325 | A | 10/1974 | Pickard |
| 3,944,018 | A | 3/1976 | Satory |
| 4,048,453 | A | 9/1977 | Seidel |
| 4,065,176 | A | 12/1977 | Fontana |
| 4,133,053 | A | 1/1979 | Lundin |
| 4,277,847 | A | 7/1981 | Florio |
| 4,349,081 | A | 9/1982 | Pepple |
| D266,417 | S | 10/1982 | Perez |
| 4,391,000 | A | 7/1983 | Lonnstedt |
| 4,404,434 | A | 9/1983 | Pelt et al. |
| 4,409,442 | A | 10/1983 | Kamimura |
| 4,445,005 | A | 4/1984 | Furuhashi |
| 4,455,457 | A | 6/1984 | Akira |
| 4,463,223 | A | 7/1984 | Yamanoi et al. |
| 4,471,496 | A | 9/1984 | Gardner, Jr. et al. |
| 4,486,903 | A | 12/1984 | Krystal |
| 4,499,593 | A | 2/1985 | Antle |
| 4,516,274 | A | 5/1985 | Buckland |
| 4,542,803 | A | 9/1985 | Houng |
| 4,546,215 | A | 10/1985 | Ferraro |
| 4,571,746 | A | 2/1986 | Gorike |
| 4,609,786 | A | 9/1986 | Omoto et al. |
| 4,615,185 | A | 10/1986 | Bollinger |
| 4,633,530 | A | 1/1987 | Satterfield |
| 4,654,898 | A | 4/1987 | Ishikawa |
| 4,660,229 | A | 4/1987 | Harris |
| 4,662,590 | A | 5/1987 | Hungerford, Jr. |
| 4,669,129 | A | 6/1987 | Chance |
| 4,670,911 | A | 6/1987 | Dunford |
| 4,682,374 | A | 7/1987 | Geiser |
| 4,713,843 | A | 12/1987 | Duncan |
| 4,727,599 | A | 2/1988 | Rappaport et al. |
| 4,747,145 | A | 5/1988 | Wiegel |
| 4,776,042 | A | 10/1988 | Hanson et al. |
| 4,776,044 | A * | 10/1988 | Makins ............ 2/209.13 |
| 4,783,822 | A | 11/1988 | Toole et al. |
| 4,791,684 | A | 12/1988 | Schwartz |

(56) References Cited

U.S. PATENT DOCUMENTS

| | | | |
|---|---|---|---|
| 4,796,307 A | 1/1989 | Vantine | |
| 4,802,245 A | 2/1989 | Miano | |
| 4,805,239 A | 2/1989 | Ciago | |
| D301,477 S | 6/1989 | Storyk | |
| 4,845,751 A | 7/1989 | Schwab | |
| 4,850,055 A | 7/1989 | Hwang | |
| 4,858,248 A | 8/1989 | Goldsmith et al. | |
| 4,864,619 A | 9/1989 | Spates | |
| 4,872,219 A | 10/1989 | Duncan | |
| 4,907,266 A | 3/1990 | Chen | |
| 4,918,757 A | 4/1990 | Janssen et al. | |
| 4,930,148 A | 5/1990 | Lee | |
| 4,969,069 A | 11/1990 | Eichost | |
| 4,982,451 A | 1/1991 | Graham | |
| 5,003,589 A | 3/1991 | Chen | |
| 5,033,094 A | 7/1991 | Hung | |
| 5,035,005 A | 7/1991 | Hung | |
| 5,038,412 A * | 8/1991 | Cionni | 2/209 |
| 5,046,192 A | 9/1991 | Ryder | |
| 5,052,194 A | 10/1991 | Jarus | |
| 5,056,161 A | 10/1991 | Breen | |
| 5,086,789 A | 2/1992 | Tichy | |
| 5,095,382 A | 3/1992 | Abe | |
| 5,113,428 A | 5/1992 | Fitzgerald | |
| 5,117,464 A | 5/1992 | Jones et al. | |
| 5,117,465 A | 5/1992 | MacDonald | |
| 5,164,987 A | 11/1992 | Raven | |
| 5,201,856 A * | 4/1993 | Edwards | 2/209 |
| 5,257,420 A * | 11/1993 | Byrne, Jr. | 2/209 |
| 5,265,165 A | 11/1993 | Rauch | |
| 5,285,530 A | 2/1994 | Nardone, Jr. | |
| 5,293,647 A | 3/1994 | Mirmilshteyn et al. | |
| D346,380 S | 4/1994 | Fitzgerald | |
| 5,303,426 A | 4/1994 | Jones | |
| 5,327,178 A | 7/1994 | McManigal | |
| 5,339,467 A | 8/1994 | Brinkley | |
| 5,357,585 A | 10/1994 | Kumar | |
| 5,395,400 A * | 3/1995 | Stafford et al. | 607/109 |
| 5,410,735 A | 4/1995 | Borchardt et al. | |
| 5,509,146 A | 4/1996 | Bryerton, Sr. | |
| 5,528,774 A | 6/1996 | Sanders | |
| 5,545,859 A | 8/1996 | Ullrich | |
| 5,551,089 A * | 9/1996 | Whidden | 2/209 |
| 5,551,090 A | 9/1996 | Thompson | |
| 5,567,038 A | 10/1996 | Lary | |
| D375,825 S | 11/1996 | Whidden | |
| 5,617,589 A | 4/1997 | Lacore et al. | |
| 5,625,903 A | 5/1997 | Schultz et al. | |
| 5,673,438 A | 10/1997 | Lambert | |
| 5,691,515 A | 11/1997 | Landis | |
| 5,708,725 A | 1/1998 | Ito | |
| D390,564 S | 2/1998 | Savona | |
| 5,718,001 A * | 2/1998 | Wright | 2/209 |
| 5,721,775 A | 2/1998 | Leifer | |
| 5,724,119 A | 3/1998 | Leight | |
| 5,749,099 A | 5/1998 | Voorhees | |
| 5,793,878 A | 8/1998 | Chang | |
| 5,821,468 A | 10/1998 | Urella et al. | |
| 5,835,609 A * | 11/1998 | LeGette et al. | 381/385 |
| 5,860,166 A | 1/1999 | Ritts | |
| 5,881,390 A | 3/1999 | Young | |
| 5,887,286 A | 3/1999 | Waldron | |
| 5,898,945 A | 5/1999 | Weiser | |
| 5,943,703 A | 8/1999 | Avila, Jr. | |
| 5,951,141 A | 9/1999 | Bradley | |
| 5,953,434 A | 9/1999 | Boyden | |
| 6,016,574 A | 1/2000 | Chen | |
| 6,029,282 A | 2/2000 | Buschman | |
| 6,055,672 A | 5/2000 | Natvig | |
| 6,065,157 A | 5/2000 | Felman | |
| 6,095,146 A | 8/2000 | Knauer et al. | |
| 6,104,824 A | 8/2000 | Ito | |
| 6,131,204 A | 10/2000 | Otey | |
| 6,148,446 A | 11/2000 | Leight | |
| 6,212,282 B1 | 4/2001 | Mershon | |
| 6,237,157 B1 | 5/2001 | Lobbins | |
| 6,298,493 B1 * | 10/2001 | Ambroise | 2/209 |
| 6,332,223 B1 * | 12/2001 | Le Gette et al. | 2/209 |
| 6,369,958 B1 | 4/2002 | Himmele | |
| 6,373,942 B1 | 4/2002 | Braund | |
| 6,377,697 B1 | 4/2002 | Cheng | |
| 6,392,196 B1 | 5/2002 | Lin | |
| 6,406,811 B1 | 6/2002 | Hall et al. | |
| 6,466,681 B1 | 10/2002 | Siska, Jr. et al. | |
| 6,499,146 B2 | 12/2002 | Bavetta et al. | |
| 6,502,247 B2 * | 1/2003 | Le Gette et al. | 2/209 |
| 6,502,248 B2 * | 1/2003 | LeGette et al. | 2/209 |
| D473,539 S | 4/2003 | O'Leary | |
| 6,580,800 B1 | 6/2003 | Yamasaki et al. | |
| 6,678,897 B2 | 1/2004 | Lindgren | |
| 6,735,784 B2 * | 5/2004 | Isom et al. | 2/209 |
| 6,744,901 B2 | 6/2004 | Ito et al. | |
| 6,873,862 B2 | 3/2005 | Reshefsky | |
| 6,880,174 B2 * | 4/2005 | Prokop | 2/209 |
| 6,888,950 B2 * | 5/2005 | Siskin et al. | 381/378 |
| 6,918,678 B2 | 7/2005 | McClanahan | |
| 6,920,645 B2 | 7/2005 | LeGette et al. | |
| 6,944,886 B1 * | 9/2005 | Jackson | 2/209 |
| 6,965,681 B2 | 11/2005 | Almqvist | |
| 6,978,483 B2 * | 12/2005 | Isom et al. | 2/209 |
| 6,980,165 B2 | 12/2005 | Yuasa et al. | |
| 7,020,902 B1 | 4/2006 | Tyler | |
| 7,024,013 B1 * | 4/2006 | Van Dam et al. | 381/376 |
| 7,072,483 B2 | 7/2006 | Lenhard-Backhaus | |
| 7,114,823 B2 | 10/2006 | McCullough et al. | |
| 7,165,272 B2 | 1/2007 | Hudson et al. | |
| D541,482 S | 4/2007 | LeGette et al. | |
| 7,210,173 B2 * | 5/2007 | Bavetta et al. | 2/209 |
| 7,212,645 B2 * | 5/2007 | Le Gette et al. | 381/370 |
| 7,222,373 B2 * | 5/2007 | Healy et al. | 2/209 |
| D545,001 S | 6/2007 | LeGette et al. | |
| 7,318,654 B2 | 1/2008 | McClanahan | |
| 7,377,666 B1 | 5/2008 | Tyler | |
| 7,424,125 B2 | 9/2008 | Amae et al. | |
| 7,548,617 B2 | 6/2009 | Yuen | |
| 7,614,091 B2 | 11/2009 | LeGette et al. | |
| 7,617,543 B2 | 11/2009 | LeGette et al. | |
| 7,650,649 B2 | 1/2010 | Le Gette et al. | |
| 7,962,970 B2 | 6/2011 | Le Gette et al. | |
| 7,996,923 B2 | 8/2011 | Isom et al. | |
| 8,204,265 B2 * | 6/2012 | Siskin et al. | 381/334 |
| 8,325,961 B2 * | 12/2012 | Le Gette et al. | 381/370 |
| 2001/0017925 A1 | 8/2001 | Ceravolo | |
| 2002/0172390 A1 | 11/2002 | Roberts | |
| 2003/0037366 A1 | 2/2003 | Lindgren | |
| 2003/0140397 A1 | 7/2003 | Isom et al. | |
| 2004/0005071 A1 * | 1/2004 | Siskin et al. | 381/378 |
| 2004/0187192 A1 * | 9/2004 | Isom et al. | 2/209 |
| 2004/0252487 A1 | 12/2004 | McCullough et al. | |
| 2005/0028250 A1 | 2/2005 | Zaic | |
| 2005/0034216 A1 * | 2/2005 | Le Gette et al. | 2/209 |
| 2005/0034217 A1 * | 2/2005 | Healy et al. | 2/209 |
| 2005/0100184 A1 | 5/2005 | Siskin et al. | |
| 2005/0246815 A1 | 11/2005 | LeGette et al. | |
| 2005/0283882 A1 | 12/2005 | Berger et al. | |
| 2006/0000006 A1 | 1/2006 | Gellis et al. | |
| 2007/0154029 A1 | 7/2007 | Werner | |
| 2007/0160249 A1 | 7/2007 | LeGette et al. | |
| 2007/0199133 A1 | 8/2007 | Bavetta et al. | |
| 2007/0226876 A1 | 10/2007 | Foust et al. | |
| 2008/0044052 A1 | 2/2008 | Whipple | |
| 2008/0141439 A1 | 6/2008 | Healy et al. | |
| 2008/0181429 A1 | 7/2008 | Fried | |
| 2008/0216214 A1 | 9/2008 | Dolby | |
| 2008/0279403 A1 | 11/2008 | Pedersen et al. | |
| 2008/0307562 A1 | 12/2008 | Tipp | |
| 2008/0307563 A1 | 12/2008 | LeGette et al. | |
| 2008/0307564 A1 | 12/2008 | LeGette et al. | |
| 2008/0307565 A1 | 12/2008 | LeGette et al. | |
| 2009/0013447 A1 | 1/2009 | Drosihn | |
| 2009/0013448 A1 | 1/2009 | Drosihn | |
| 2009/0154740 A1 | 6/2009 | Regen et al. | |
| 2009/0196453 A1 | 8/2009 | Amae et al. | |

(56) References Cited

U.S. PATENT DOCUMENTS

| | | |
|---|---|---|
| 2009/0205110 A1 | 8/2009 | Chiang |
| 2010/0175165 A1 | 7/2010 | Le Gette |
| 2011/0119804 A1 | 5/2011 | Chiang |

FOREIGN PATENT DOCUMENTS

| | | |
|---|---|---|
| CH | 662052 | 9/1987 |
| CN | 2291138 | 9/1998 |
| CN | 2353337 Y | 12/1999 |
| DE | 483279 | 9/1929 |
| DE | 641554 | 2/1937 |
| DE | 2516709 A1 | 10/1976 |
| DE | 3231218 A1 | 2/1984 |
| DE | 4422767 A1 | 1/1996 |
| DE | 29800973 U1 | 4/1998 |
| DE | 29812652 U1 | 3/1999 |
| DE | 20003363 U1 | 8/2000 |
| DE | 201 10 028 | 8/2001 |
| EP | 126690 A1 | 11/1984 |
| EP | 0745364 | 8/2002 |
| FR | 1353524 | 1/1963 |
| FR | 2280283 | 2/1976 |
| FR | 2536253 A1 | 11/1982 |
| FR | 2538204 A1 | 12/1982 |
| FR | 2532838 A1 | 9/1983 |
| GB | 1327614 | 8/1973 |
| GB | 1 508 101 | 4/1978 |
| GB | 2059206 A | 4/1981 |
| GB | 2062478 | 5/1981 |
| GB | 2226931 A | 7/1990 |
| GB | 2290696 A | 1/1996 |
| GB | 2320885 | 8/1998 |
| GB | 2339642 | 2/2000 |
| JP | S49-03517 | 4/1972 |
| JP | 47-19024 | 11/1972 |
| JP | 48-75626 | 9/1973 |
| JP | S54-44016 | 9/1977 |
| JP | 53-066098 | 6/1978 |
| JP | 53-143627 | 11/1978 |
| JP | 55-50653 | 4/1980 |
| JP | 56-146719 U | 11/1981 |
| JP | 56-164218 U | 12/1981 |
| JP | 57-11884 | 1/1982 |
| JP | 60-29141 | 2/1982 |
| JP | 57-205216 | 12/1982 |
| JP | 58-15618 | 1/1983 |
| JP | 58-37289 U | 3/1983 |
| JP | 58-54191 U | 4/1983 |
| JP | 58-138484 | 9/1983 |
| JP | 58-182594 U | 12/1983 |
| JP | 59-128149 | 8/1984 |
| JP | 59-129815 | 8/1984 |
| JP | 56-194205 | 12/1984 |
| JP | 60-94635 | 6/1985 |
| JP | 60-244188 | 12/1985 |
| JP | 62-21016 | 2/1987 |
| JP | 63-20232 | 6/1988 |
| JP | 1068506 A | 3/1989 |
| JP | 1068508 A | 3/1989 |
| JP | 1-125319 | 8/1989 |
| JP | 1-125320 U | 8/1989 |
| JP | 05-207581 | 8/1993 |
| JP | 6-41720 | 6/1994 |
| JP | 6-351090 | 12/1994 |
| JP | 07-213403 | 8/1995 |
| JP | 10-079994 | 3/1998 |
| JP | 10-85251 | 7/1998 |
| JP | 3053142 U | 10/1998 |
| JP | 11-089699 | 4/1999 |
| JP | 11-229223 | 8/1999 |
| JP | 10257581 | 8/2000 |
| JP | 3082758 | 12/2001 |
| JP | 2002-11036 | 1/2002 |
| KR | 20-0226271 | 3/2001 |
| KR | 20-0314976 | 6/2003 |
| KR | 30-0336877 | 11/2003 |
| KR | 20-357405 | 7/2004 |
| KR | 20-357406 | 7/2004 |
| KR | 10/0703878 | 4/2007 |
| SE | 452237 B | 11/1987 |
| WO | 92/17079 A1 | 10/1992 |
| WO | 94/02043 A1 | 2/1994 |
| WO | 94/09734 A1 | 5/1994 |
| WO | 97/48296 A1 | 12/1997 |
| WO | 98/07062 A1 | 2/1998 |
| WO | 98/31314 A1 | 7/1998 |
| WO | 01/76402 A1 | 10/2001 |
| WO | 02/053061 A3 | 7/2002 |
| WO | 02/083044 A1 | 10/2002 |
| WO | 03/086124 A1 | 10/2003 |
| WO | 2010/017359 A1 | 2/2010 |

OTHER PUBLICATIONS

"Hearmuff: Fleece headwear with internal stereo headphones" from http://www.hearmuff.com/index.htm, 2003, 1 page.

Photographs of Yukon Cornelius Product, undated, 3 pages.

Opinion from the District Court of Maryland in *180s, Inc. and 180s, LLC* v. *Gordini U.S.A., Inc.* (Case 1:08-cv-00177-JFM), 23 pages, dated Mar. 30, 2010.

1999-2000 Catalog "Accessory Goods"—Nitty Company, Ltd. 4 pgs.

Chicago Tribune article entitled "Winter From Head to Toe Lend an Ear to the Tale of this Intrepid Inventor", by Sid Moody, Feb. 16, 1988, 4 pgs.

History of the United States Patent Office—The Patent Office Pony—A History of the Early Patent Office, by Kenneth W. Dobyns, 1994, [Introductory Material—3pgs.; Chapter 29—4 pgs.; and Sources and Annotations—40 pgs.].

2003 Catalog, "Join the Polar Fusion Revolution; Revolutionary Ear Warmers," Polar Fusion LLC.—2 pgs.

Nitty Company Ltd. Winter '89-'90 catalog, 6 pages.

Nitty Company Ltd., Winter '90-'91 catalog, 4 pages.

Defendant Gordini's First Supplemental and Amended Answers and Objections to Plaintiff's Second Set of Interrogatories (Non-Confidential Version) from *180s, Inc. and 180s, LLC* v. *Gordini U.S.A., Inc.* (Case 1:08-cv-00177-JFM), 29 pages, dated Feb. 4, 2009.

"Hearmuffs" from http://www.hearmuff.com/goods.htm, 2003, 2 pgs.

"Hearmuffs" from http://www.hearmuff.com/about.htm, 2003, 3 pgs.

Search Report for European Application No. EP 01 99 1215, 2 pages, dated Jun. 1, 2004.

Office Action for Canadian Patent Application No. 2,858,544, mailed Apr. 29, 2015.

Case 1:13-cv-03239-JFM, Document 43, Costco Wholesale Corporation's First Amended Answer to the Complaint and First Amended Counterclaims, U.S. District Court, District of Maryland, Feb. 4, 2014.

Case 1:13-cv-03239-JFM, Document 44, SM Global,LLC's First Amended Answer to the Complaint and First Amended Counterclaims, U.S. Court, District of Maryland, Feb. 4, 2014.

\* cited by examiner

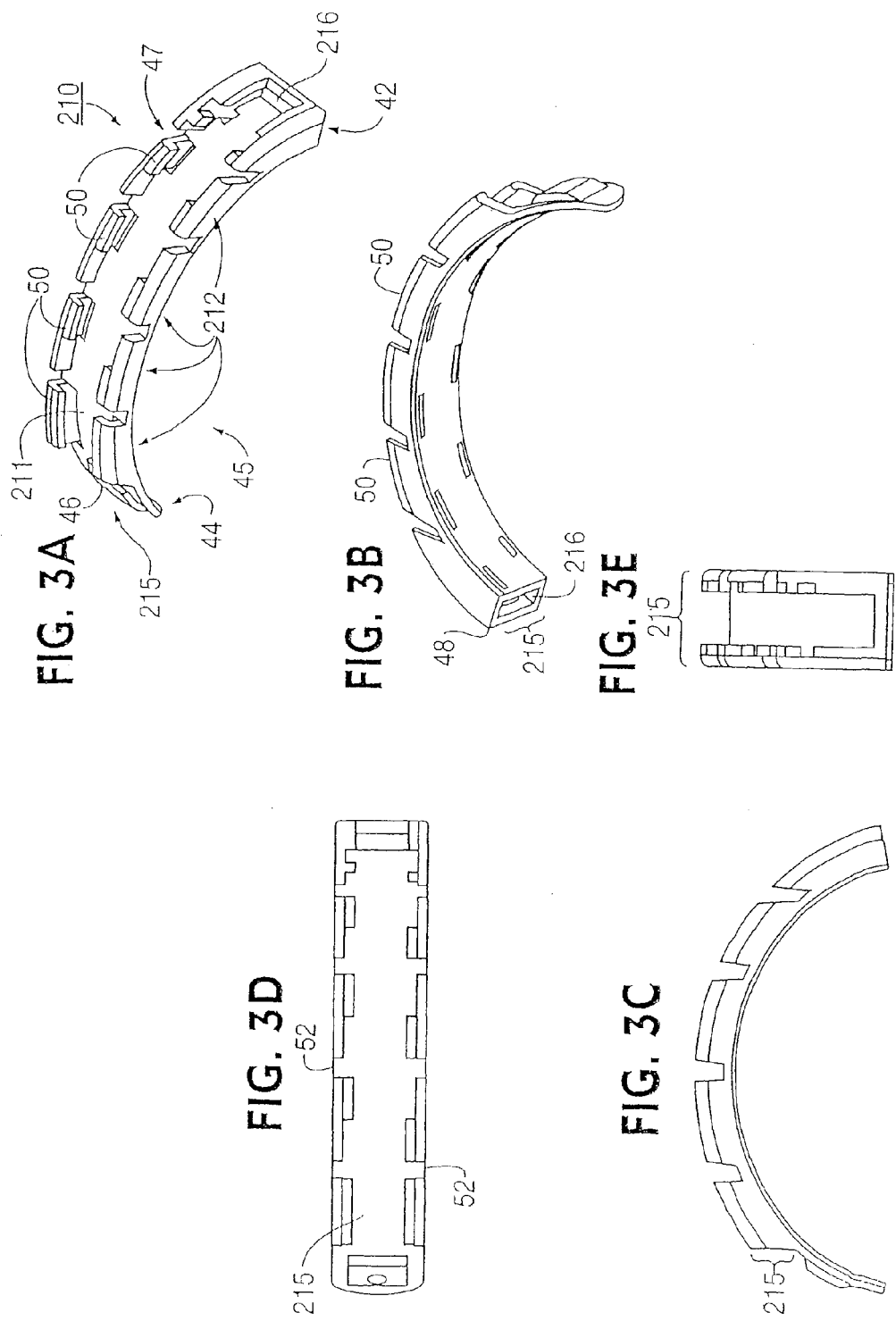

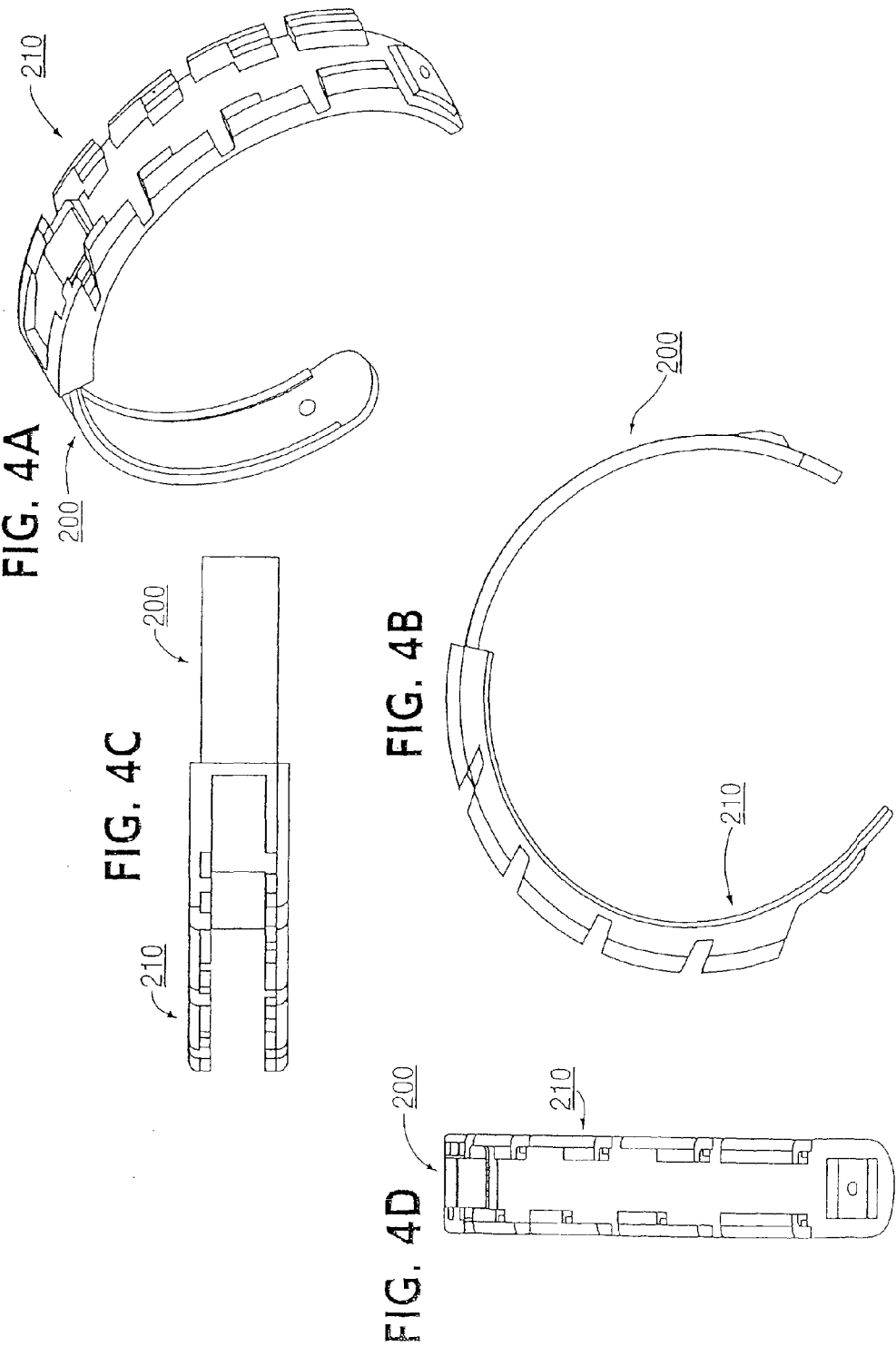

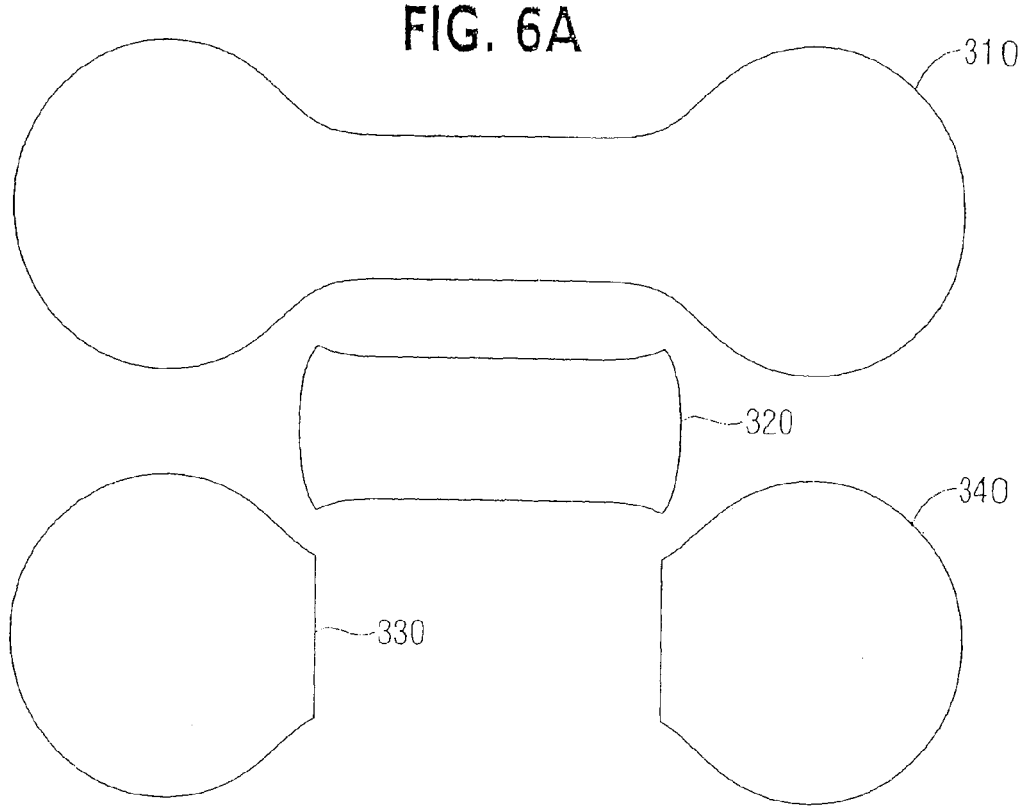
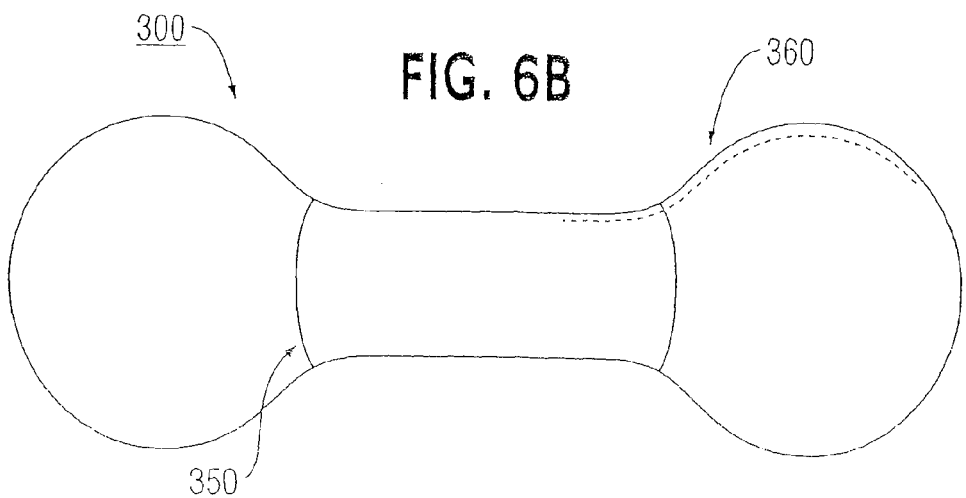

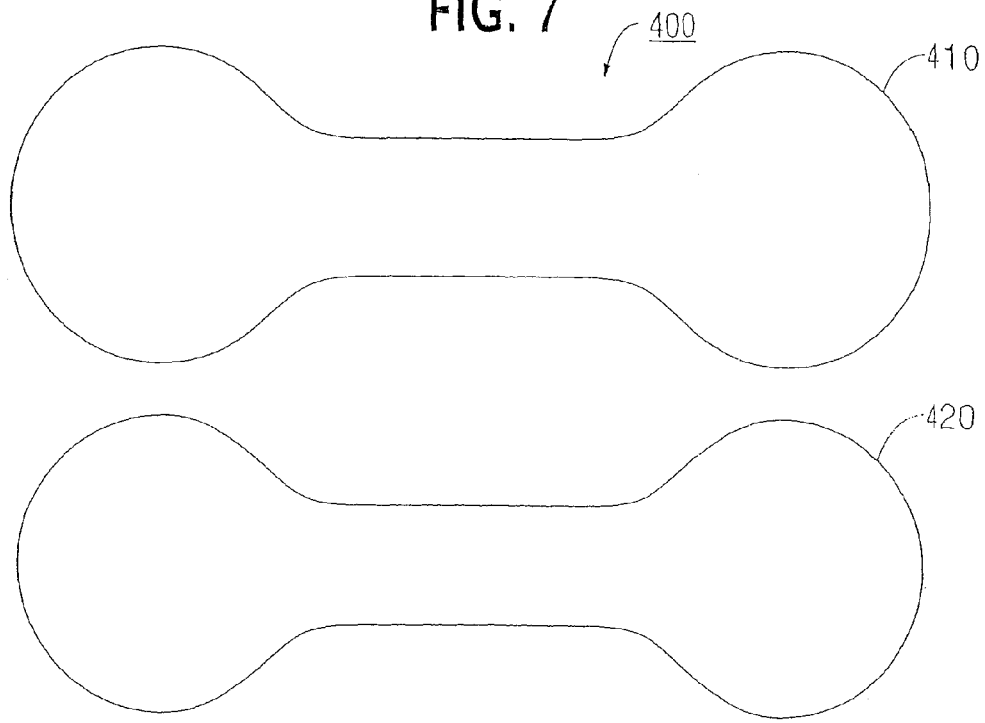
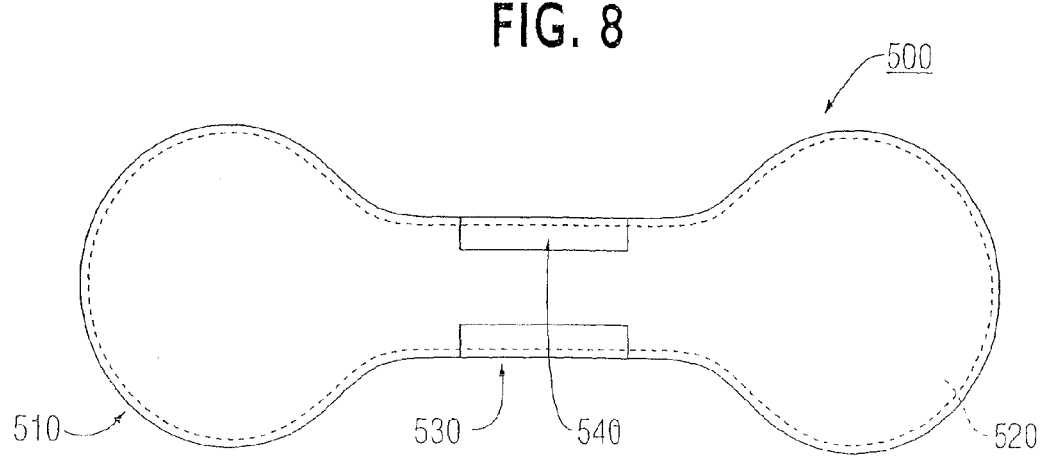

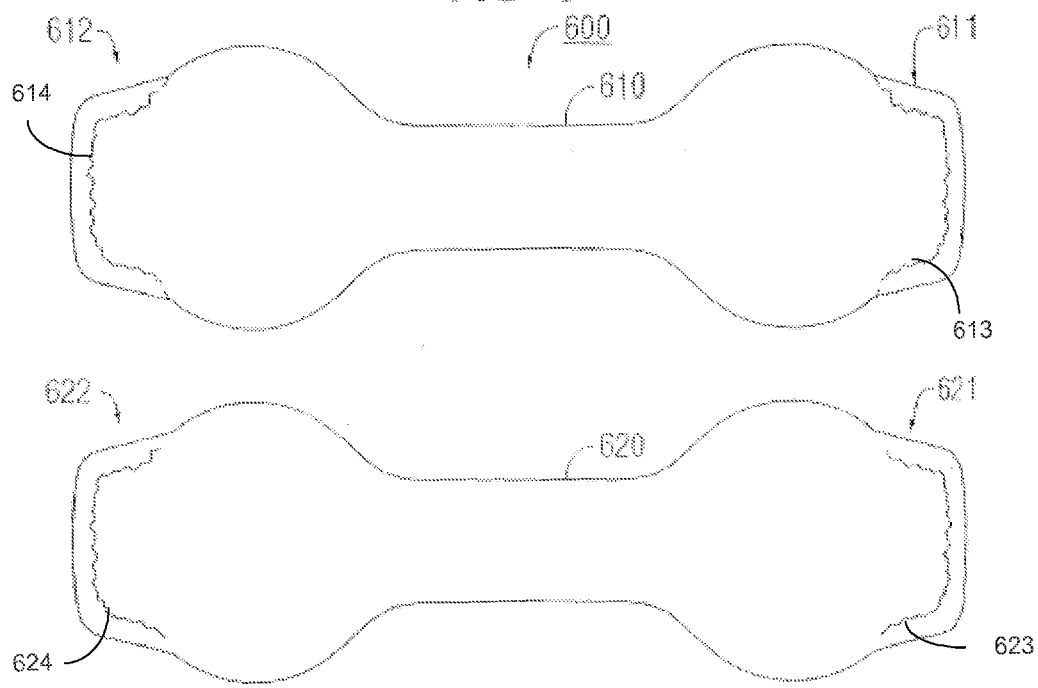
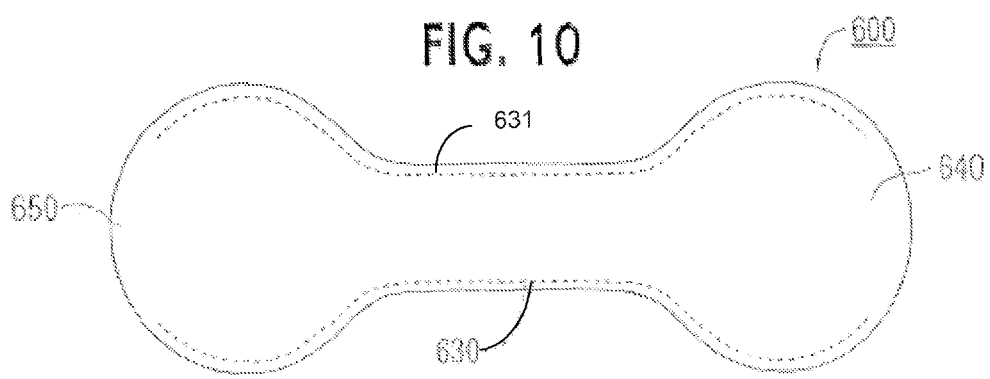

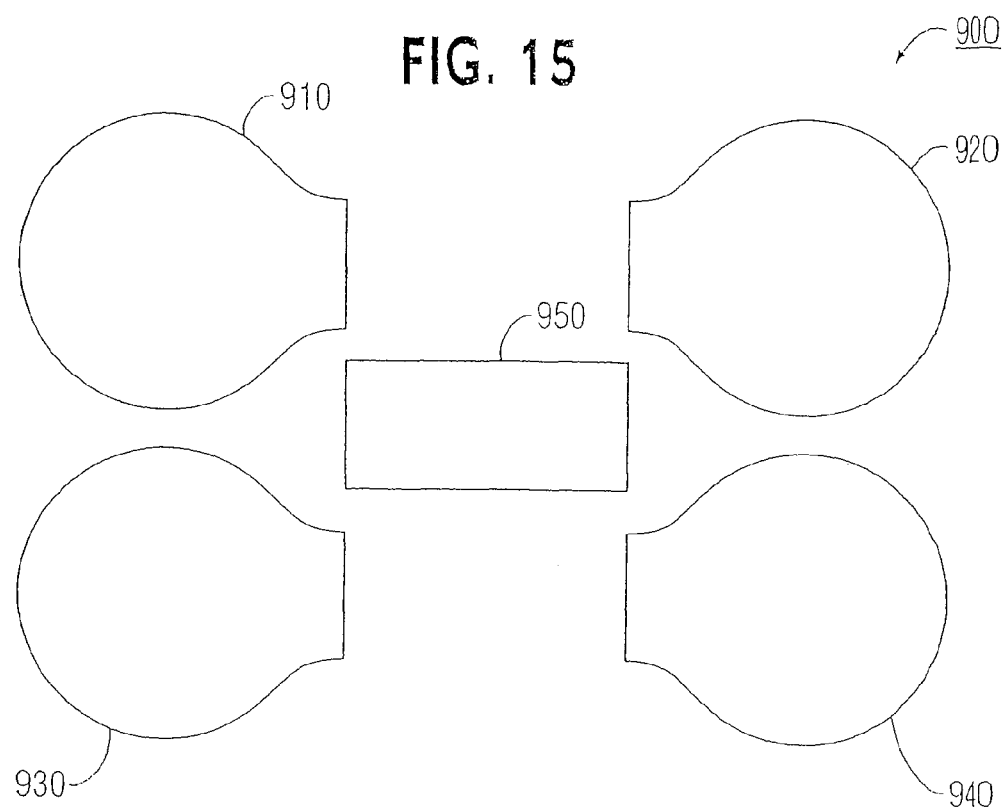
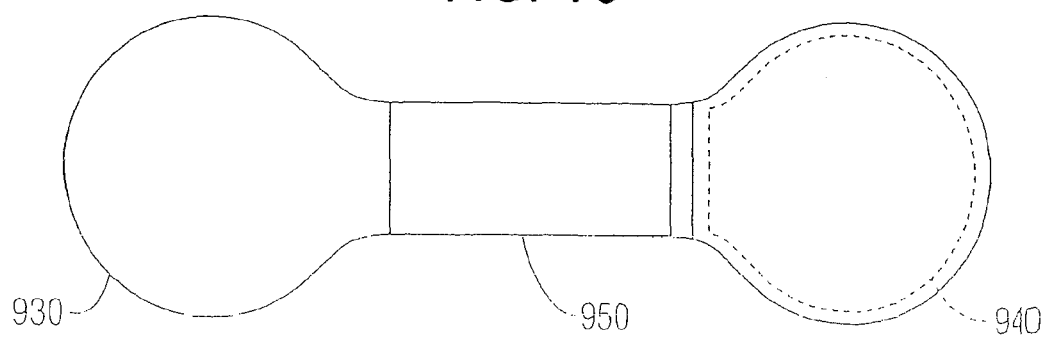

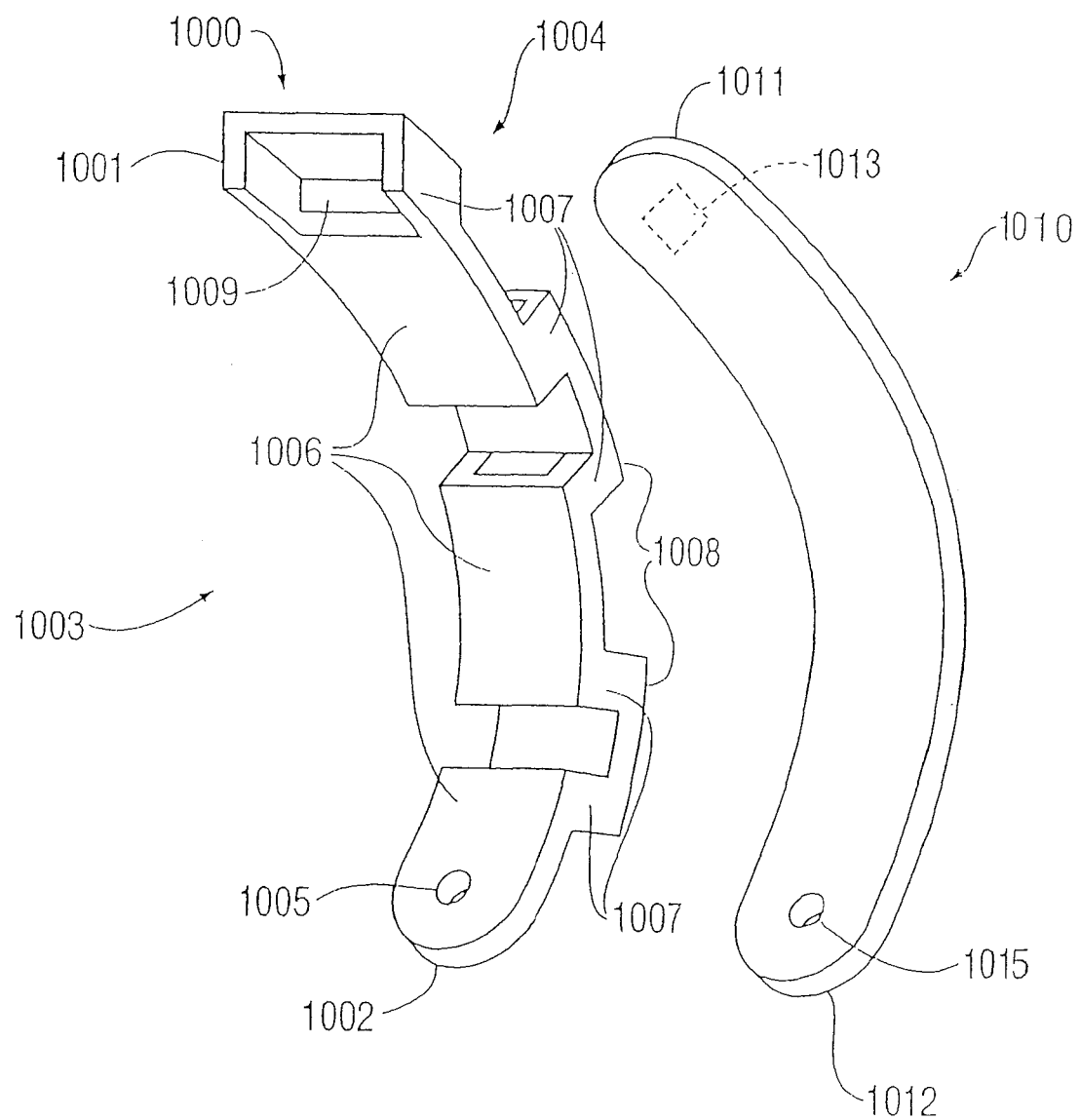

EAR PROTECTION DEVICE

CROSS-REFERENCE TO RELATED APPLICATIONS

The present application is a continuation of U.S. patent application Ser. No. 11/742,181, entitled "Ear Protection Device," filed Apr. 30, 2007, which is a continuation of U.S. patent application Ser. No. 11/108,614, entitled "Ear Protection Device," filed Apr. 18, 2005, now U.S. Pat. No. 7,210,173, issued May 1, 2007, which is a continuation of U.S. patent application Ser. No. 10/330,213, entitled "Ear Protection Device," filed Dec. 30, 2002, now U.S. Pat. No. 6,880,174, issued Apr. 19, 2005, which is a continuation of U.S. patent application Ser. No. 10/024,523, entitled "Ear Protection Device," filed Dec. 21, 2001, now U.S. Pat. No. 6,499,146, issued Dec. 31, 2002, which claims priority to and is related to U.S. Provisional Patent Application No. 60/259,114, entitled "Ear Covering," filed Dec. 29, 2000. The entire disclosure of each of the above-identified patent applications is incorporated herein by reference.

The present application is also related to U.S. application Ser. Nos. 09/521,241 and 09/978,591, now U.S. Pat. Nos. 6,332,223 and 6,502,247 respectively, both of which are entitled "Apparatus and Method for Making an Ear Warmer Having Interior Seams," the entire disclosures of which are incorporate herein by reference.

BACKGROUND OF THE INVENTION

The invention in general relates to an ear protection device. More specifically, the invention relates to an ear protection device with adjustable bands.

Ear muffs that are worn over the top or around the back of a user's head are generally known. For example, U.S. Pat. No. 1,628,483 to Wiegand discloses an ear protector. The ear protector includes a pair of oval-shaped plates, each plate being formed with an inwardly extending continuous flaring flange. The flange provides a conical profile. The plates are connected together via slidably connected resilient arms. The ear protector includes a hold fast device or rivet for coupling each of the resilient arms to a respective oval plate. The resilient arms each include a band for slidably receiving the other overlapping resilient arm. The bands hold the resilient arms together and allow for the sliding movement between the two resilient arms to allow the ear protector to be adjusted for a specific user. The ear protector can be worn with the resilient arms extending around the back of the head.

This known ear muff, however, does not effectively maintain its position on a user's head. In addition, this ear muff does not allow a fabric member to cover entirely the frame structure of the ear muff.

Thus, a need exists for frames for ear protection devices that maintain their position on a user's head. In addition, a need exists for a shell (e.g., made of fabric) that entirely covers the ear-protect ion-device frame.

SUMMARY OF THE INVENTION

An apparatus comprising a first curved band portion and a second curved band portion. The first curved band portion has a first end, a second end, an inner curved side and an outer curved side. The first curved band portion defines a passageway between the first end and the second end of the first curved band portion. The passageway has a first opening. The second curved band portion has a first end, a second end, an inner curved side and an outer curved side. A motion-restraint portion is proximate to the first end of the second curved band portion. The first end of the second curved band portion is insertable into the first opening of the passageway of the first curved band portion. The first curved band portion has a range of motion within the passageway of the second curved band portion.

BRIEF DESCRIPTION OF THE DRAWINGS

FIGS. 3A-3E show a top perspective view, bottom perspective view, a side view, a top view and a front view, respectively, of a second band portion, according to an embodiment of the invention.

FIGS. 4A-4D show a perspective view, a side view, a rear view and a front view, respectively, of two band portions, according to an embodiment of the invention.

FIG. 6A shows a top view of shell membranes, according to an embodiment of the invention.

FIG. 6B shows a top view of the shell membranes shown in FIG. 6A while assembled into a shell.

FIG. 7 shows a top view of shell membranes, according to another embodiment of the invention.

FIG. 8 shows a top view of an assembled shell, according to another embodiment of the invention.

FIG. 9 shows a top view of shell membranes, according to another embodiment of the invention.

FIG. 10 shows a top view of shell membranes of FIG. 9 partially sewn during an immediate step of assembling an ear protection device.

FIG. 15 shows a top view of shell membranes, according to another embodiment of the invention.

FIG. 16 shows a top view of an assembled shell based on the shell membranes shown in FIG. 15.

FIG. 17 shows a perspective view of two band portions, according to an embodiment of the invention.

DETAILED DESCRIPTION

Figure 1:
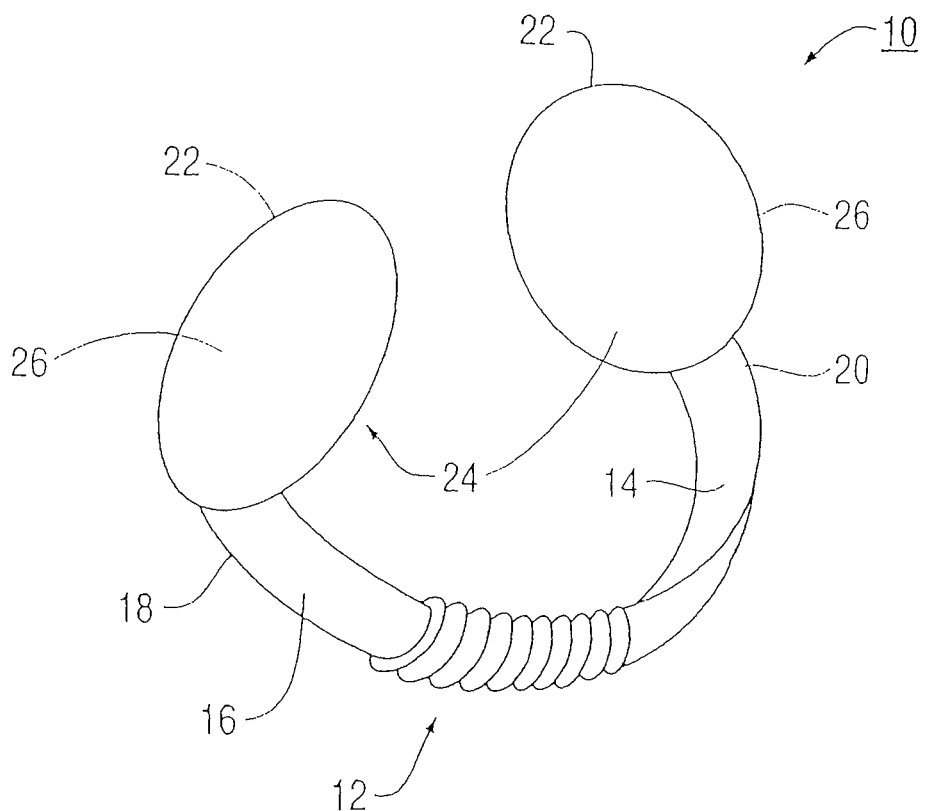
FIG. 1 shows a perspective view of an ear protection device, according to an embodiment of the invention.
Figure 2A:
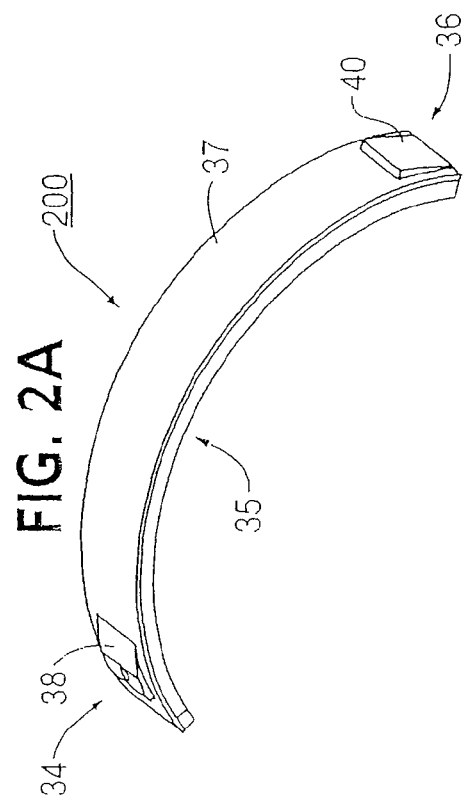
FIGS. 2A-2D show a perspective view, a side view, a top view and a front view, respectively, of a first band portion, according to an embodiment of the invention.
Figure 2D:
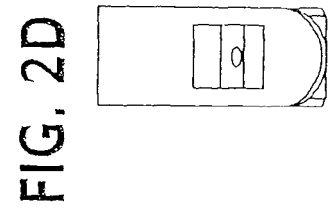
Figure 2C:
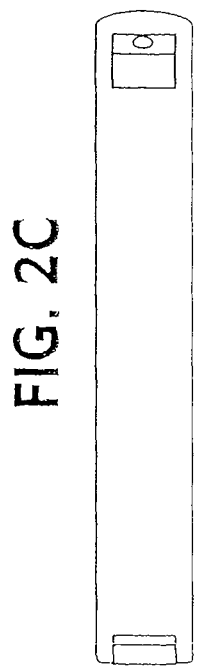
Figure 2B:
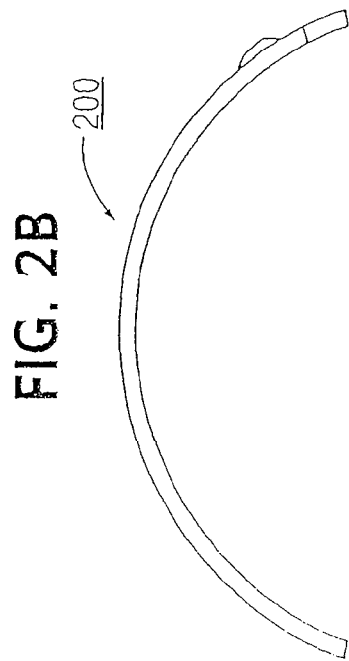

FIG. 1 shows a perspective view of an ear protection device, according to an embodiment of the invention. As shown in FIG. 1, the ear protection device 10 includes a head band portion 12 having an inner side 14 and an outer side 16.

Ear protection device 10 also includes a first end portion 18 and a second end portion 20. The first end portion 18 and second end portion 20 are connected to respective ear portions 22. Each ear portion 22 has an inner side 24 and an outer side 26. The ear protection device 10 is covered in a textile material, such as fleece. Note that the head band portion 12 is covered by excess material that gathers.

FIGS. 2A-2D show a perspective view, a side view, a top view and a front view, respectively, of a first band portion, according to an embodiment of the invention. Band portion 200 includes a first end 34, a second end 36, an inner side 35 and an outer side 37. Band portion 200 includes a raised mounting surface 38 disposed at the outer side 37 and proximate to the first end 34. Band portion 200 also includes a motion-restraint portion 40 disposed at the outer side 37 and proximate to the second end 36 of band portion 200. Although the mounting surface 38 and motion-restraint portion 40 are shown as being integrally formed with the band portion 200, they can be formed separately and attached to the band portion 200. In an alternative embodiment, the motion-restraint portion can be a detent that is integrally formed with the band portion along only a single side of the detent while the remaining sides of the detent are separated (or cut out) from the band portion.

FIGS. 3A-3E show a top perspective view, bottom perspective view, a side view, a top view and a front view, respectively, of a second band portion, according to an embodiment of the invention. Band portion 210 includes a first end 42, a second end 44, an inner side 45 and an outer side 47. Band portion 210 includes a raised mounting surface 46 disposed at the outer side 47 and proximate to the second end 44. Band portion 210 further includes a base member 211, side members 212, and upper members (or flanges) 50. The side members 212 are connected along both sides of the base member 211. The upper members 50 are connected to the side members 212 and protrude over base member 211.

The base member 211, side members 212 and upper members 50 define a passageway 215 along the band portion 210, lengthwise. In other words, the base member 211, side members 212 and upper members 50 bound a channel on various sides into which the band portion 200 can be slideably engaged. Thus, as the band portion 200 is moved through the passageway 215, the movement of band portion 200 is limited by the base member 211, side members 212 and upper members 50. The passageway 215 includes an opening 216 into which the band portion 200 can be initially inserted.

FIGS. 4A-4D show a perspective view, a side view, a rear view and a front view, respectively, of two band portions, according to an embodiment of the invention. As shown in FIGS. 4A-4D, band portion 200 is inserted into the passageway of band portion 210 through opening 216 to provide a band that has an adjustable length. More specifically, the motion-restraint portion 40 of band portion 200 is engagable with the opening 216 of passageway 215 of band portion 210. Once band portion 200 has been inserted through opening 216, the motion-restraint portion 40 engages the portions of band portion 210 that defines opening 216. This allows motion-restraint portion 40 to prevent band portion 200 from existing passageway 215 of band portion 210. Consequently, the band portion 200 has a range of motion within the passageway 215 of band portion 210 once the band portion 200 has been inserted into passageway 215 of band portion 210. This range of motion within the passageway 215 is limited on the end with the opening 216 by the engagement of motion-restraint portion 40 of band portion 210.

In an alternative embodiment, the motion-restrain portion can removably engage the passageway of the other embodiment. For example, the motion-restraint portion can be a detent integrally formed with the band portion along only a single side of the detent while the remaining sides of the detent are separated (or cut out) from the band portion. This allows the band portion to be removably inserted into the passageway of the other band portion. In other words, the detent can be depressed to disengage from the opening of the passageway thereby allowing the one band portion to be removed from the other band portion.

In another alternative embodiment, the motion-restraint portion of one band portion can at least partially engage other openings within the passageway of the other band portion. For example, the motion-restraint portion can be a detent and the upper members of the band portion that defines the passageway can extend so that they overlap slightly with the detent. This allows the detent to engage partially the openings defined by the upper members thereby causing a slight hesitation due to friction when the band portions are moved within the range of motion. Once this partial engagement is overcome, the band portions can move within the range of motion.

In yet another alternative embodiment, the upper members that define the passageway of one band portion can further extend so that the detent of the other band portion removably engages the openings defined by the upper members. In such an embodiment, the two band portions will have a range of motion that includes one or more positions where the detent removably engages the openings in the passageway. This removable engagement allows the position of the band portion to be temporarily locked within the passageway of the other band portion.

In yet another alternative embodiment, detent-engageable openings of the passageway of one band portion and the detent of the other band portion can be located on any of their respective sides. For example, the detent can be located on either side or both sides of the band portion where the detent-engagable openings of the passageway are disposed at corresponding locations on the other band portion (i.e., on the matching side or on both sides of the passageway). Alternatively, the detent can be located on the inner side the band portion where the detent-engagable openings of the passageway are disposed at corresponding location(s) on the inner side of the other band portion. In yet another embodiment, multiple detents can be located at different locations (i.e., one detent on the outer side and another detent on the inner side) of the band portion where the detent-engagable openings of the passageway are disposed at a corresponding locations on the other band portion.

Although motion-restraint portion 40 of band portion 200 is shown in FIGS. 2A-2D as a detent, other configurations are possible. For example, the motion-restraint portion can be a rivet that is coupled to the band portion once the band portion is inserted into the passageway of the other band portion. Such a rivet can be, for example, fixedly attached or removably attached to the band portion once the band portion is inserted into the passageway of the other band portion.

Figure 5:
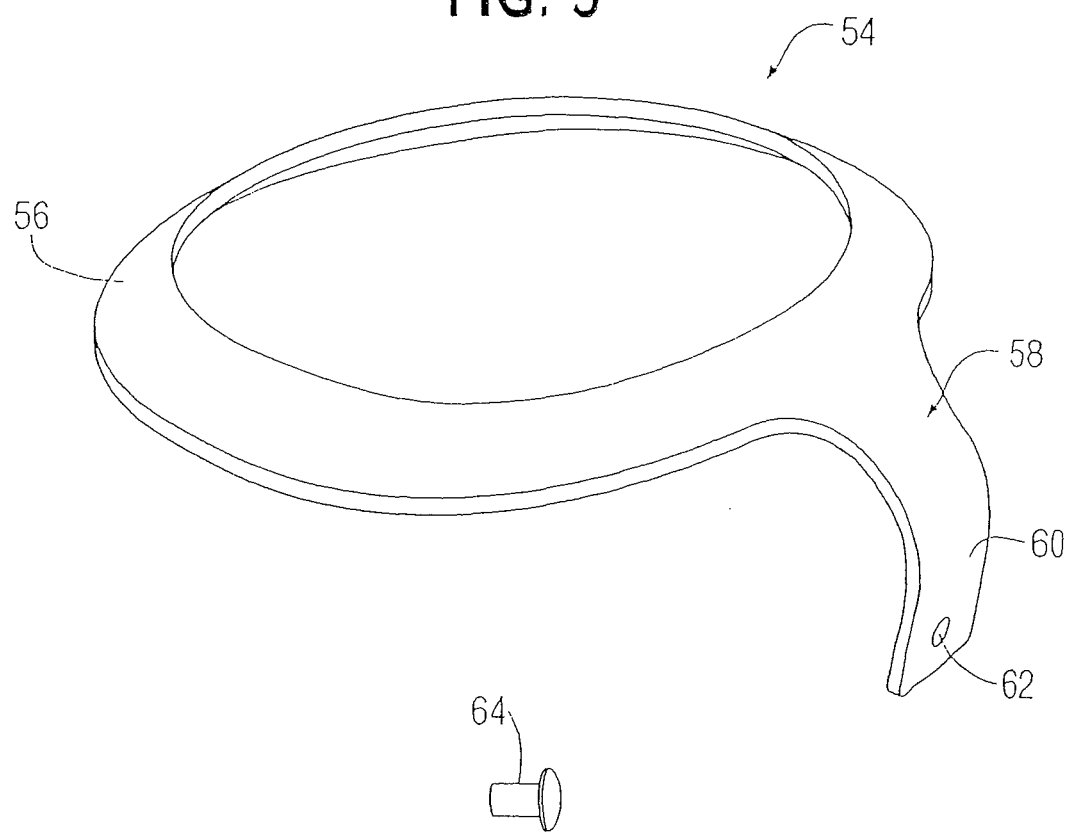
FIG. 5 shows a perspective view of an ear cup portion, according to an embodiment of the invention.

FIG. 5 shows a perspective view of an ear cup portion, according to an embodiment of the invention. As shown in FIG. 5, ear cup portion 54 includes a conical portion 56 having a transition portion 58 extending from the side of the conical portion 56. The transition portion 56 is integrally formed with mount portion 60, which includes a hole 62.

Two ear cup portions 54 can each be attached to an end of the band portions 200 and 210. In other words, one ear cup portion 54 can be attached to the raised mounting surface 38 of band portion 200 and another ear cup portion 54 can be attached to the raised mounting surface 46 of band portion 210. Ear cup portions 54 can be attached to band portions 200 and 210 by a fastener, such as for example, rivet 64. In an alternative embodiment, either the ear cup portion or the raised mounted surface of the band portions can include an integrally formed rivet for snap-action engagement with a hole in the corresponding mating structure. Note that band portions 200 and/or 210, and/or ear cup portions 54 collectively are sometimes referred to herein as a "frame."

FIG. 6A shows a top view of shell membranes, according to an embodiment of the invention. The shell membranes include outer membrane 310, inner membrane 320, and ear membranes 330 and 340. FIG. 6B shows a top view of the shell membranes shown in FIG. 6A while assembled into a shell. As shown in FIG. 6B, the membranes 310, 320, 330 and 340 can be arranged together and then sown with a seam along the perimeter. The assembled shell 300 includes two openings 350 and 360 into which portions of the frame can be inserted. For example, the band portion 200 with the attached ear cup portion 54 and be inserted into opening 350, and the band portion 210 with the attached ear cup portion 54 can be inserted into opening 360. Additional details and variations of the shell membranes are described in U.S. Pat. No. 5,835,609 to Le Gette et al. entitled "Ear Protection Device;" the disclosure of which is incorporated herein by reference.

After being inserted into shell 300, the band portions 200 and 210 can have an adjustable length to accommodate the use of the ear protection device 10 by users having different size heads or by the same user while extending over the top or around the band of that user's head. In other words, once the band portions 200 and 210 are inserted into and assembled within the shell 300, the length of the band portions 200 and 210 can be adjusted by moving band portion 200 within the passageway 215 of band portion 210.

In some embodiments, the band portions can be separated from each other while disposed within shell 300. For example, where the motion-restraint portion of one band portion is a disengageable detent, the detent can be disengaged from an opening of the passageway of the other band portion, and the band portion can be removed from the passageway of the other band portion. Then, the band portion with the attached ear cup portion 54 can be removed from shell 300 through opening 350, and the other band portion with the attached ear cup portion 54 can be removed from shell 300 through opening 360.

This allows the ear protection device 10 to have interchangeable shells. In other words, different shells can be used to cover the same frame because the band portions can be separated from each other while disposed within one shell and reassembled in another shell. Such interchangeable shells, for example, can have different colors or logos for use with a single frame.

FIG. 7 shows a top view of shell membranes, according to another embodiment of the invention. As shown in FIG. 7, the shell 400 includes outer membrane 410 and inner membrane 420. To assemble an ear protection device using shell 400, the outer membrane 410 and inner membrane 420 can be positioned over the other, with the components of the frame disposed between the two membranes 410 and 420, and then the membranes 410 and 420 can be sewn along their perimeter.

FIG. 8 shows a top view of an assembled shell, according to another embodiment of the invention. As shown in FIG. 8, the shell 500 has an inner membrane 510, outer membrane 520 and elastic membranes 530 and 540 (shown in phantom). The membranes 510, 520, 530 and 540 are sewn along the perimeter. The elastic membranes 530 and 540 can be disposed between the inner membrane 510 and the outer membrane 520. The elastic membranes 530 and 540 can form "gathers" in the central portion of the shell 500. The elastic membranes 530 and 540 can gather any additional material of membranes 510 and 520 when the ear protection device is in a configuration other than open. In other words, membranes 510 and 520 can be fully stretched when the ear protection device is in an open configuration and less than fully stretched when the ear protection device is in a closed configuration. Thus, when in the closed configuration, the elastic membranes 530 and 540 can gather membranes 510 and 520.

FIG. 9 shows a top view of shell membranes, according to another embodiment of the invention. As shown FIG. 9, the shell 600 includes outer 610 membrane and inner membrane 620. Outer membrane 610 includes end portions 611 and 612. Inner membrane 620 includes end portions 621 and 622. The end portions 611, 612, 621 and 622 can include, for example, an elastic material 613, 614, 623, 624 and can be folded over the related frame portion when assembled. The doubled-over arrangement of the end portions 611, 612, 621 and 622 can provide cushioning for the frame against the wearer's head. The elastic material 613, 614, 623, 624 can affect the appearance of the ear protection device by pulling the outer membrane 610 and inner membrane 620 tight around the perimeter of the ear cup portions of the frame. In other words, the elastic material 613, 614, 623, 624 can be pulled over the related frame portions so that the outer membrane 610 and inner membrane 620 are removeably secured to the related frame portions without being sewn along a seam.

FIG. 10 shows a top view of shell membranes of FIG. 9 partially sewn during an immediate step of assembling an ear protection device. As shown in FIG. 10, the ear protection device can be assembled by initially sewing a portion of the perimeter 630 and leaving a portion of the perimeter 640 and 650 not sewn. Two ear cup portions of the frame each can be connected to a respective band portion. Each band portion with its attached ear cup portion of the frame can then be positioned within the shell by insertion through the portions 640 and 650. The inner band portion can then be removably inserted into the passageway of the outer band (as described above, for example, in reference to FIGS. 4A-4D). In an alternative embodiment, the shell 600 can be turned inside out after the portions of perimeter 630 have been sewn.

Figure 11:
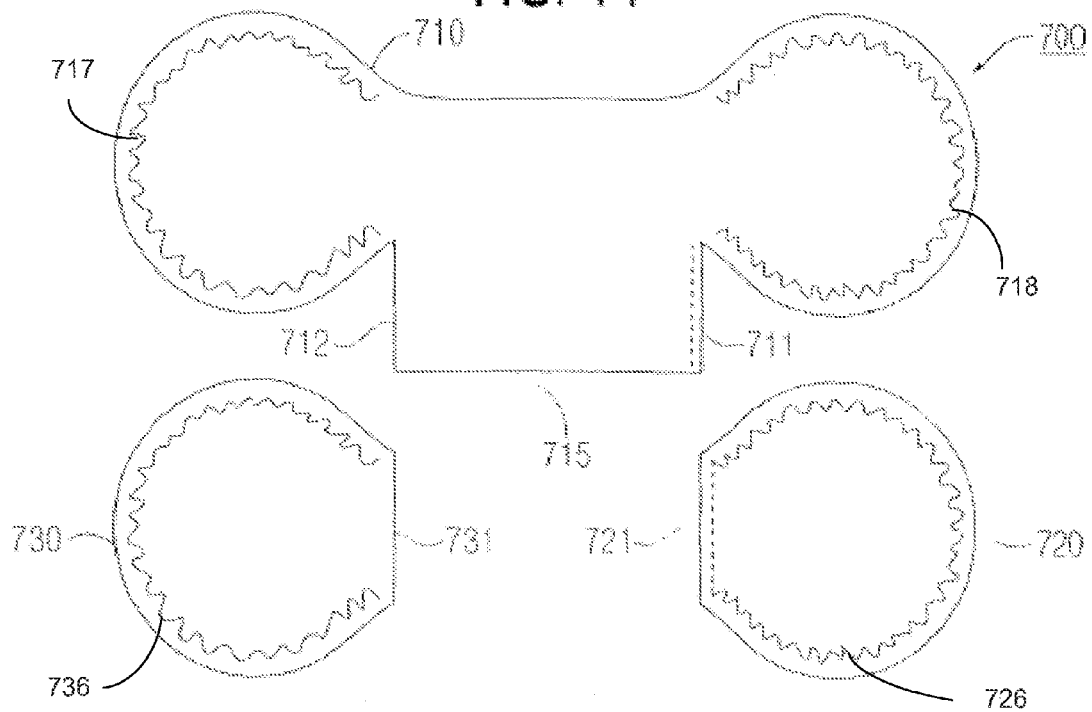
FIG. 11 shows a top view of shell membranes, according to another embodiment of the invention.

FIG. 11 shows a top view of shell membranes, according to another embodiment of the invention. The shell 700 includes outer membrane 710 and ear membranes 720 and 730. Outer membrane 710 includes middle portion 715, which is integrally formed with the remaining portions of outer membrane 710. Ear membranes 720 and 730 each have their own elastic membrane 726, 736 attached to a portion of the perimeter of the respective ear membrane. In addition, the outer membrane 710 can have its own elastic membranes 717, 718 attached to the perimeter of the ear portions of outer membrane 710. Note that although elastic membranes 717, 718, 726, 736 are shown on both the outer membrane 710 and ear membranes 720 and 730, alternative embodiments are possible where the elastic membrane is disposed at only the outer membrane or only the ear membranes.

Figure 12:
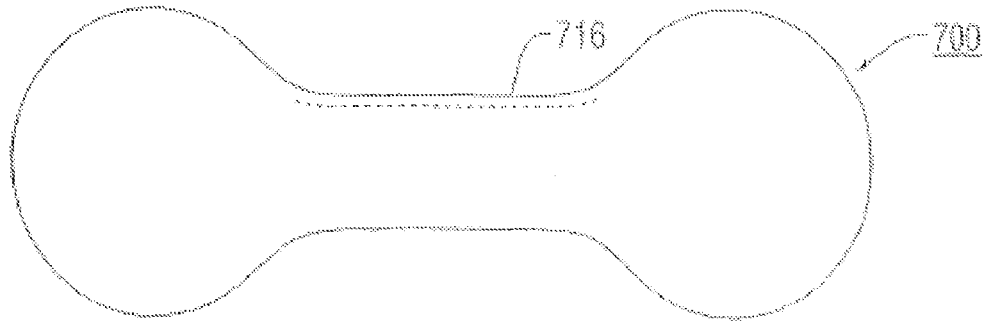
FIG. 12 shows a top view of the assembled shell based on the shell membranes shown in FIG. 11.

Shell 700 can be assembled by attaching the edge portions 721 and 731 of ear membranes 720 and 730, respectively, to portions 711 and 712 of outer membrane 710. The middle portion 715 of outer membrane 710 can be folded over and attached to the portion 716 of the outer membrane 710. This is shown in FIG. 12, which shows a top view of the assembled shell based on the shell membranes shown in FIG. 11. The ear membranes 720 and 730 optionally can be turned inside out with regards to the corresponding portions of outer membrane 710. Consequently, the attachment (e.g., a sewn seam) is disposed in the interior formed by outer membrane 710 and ear membranes 720 and 730. The frame can then be inserted into the interior formed by outer membrane 710 and ear membranes 720 and 730. The elastic membranes 717, 718, 726, 736, attached to outer membrane 710 and ear membranes 720 and 730 tend to draw the perimeter of the outer membrane 710 and ear membranes 720 and 730 inwardly. Thus, the corresponding portions of shell 700 close in around the ear cup portions of the frame. Although not shown explicitly in FIG. 12, the ear protection device will have a curvature corresponding to the shape of the frame.

In an alternative embodiment, the ear membranes need not be attached to portions of the outer membrane. Rather, the middle portion of the outer membrane can be folded over and attached. Then, the frame can be inserted into the interior formed by the outer membrane and the middle portion of the outer membrane. Finally, the ear membranes can be disposed and maintained over the ear cup portions of the frame by the elastic membranes attached to the ear membranes and the outer membrane.

Figure 13:
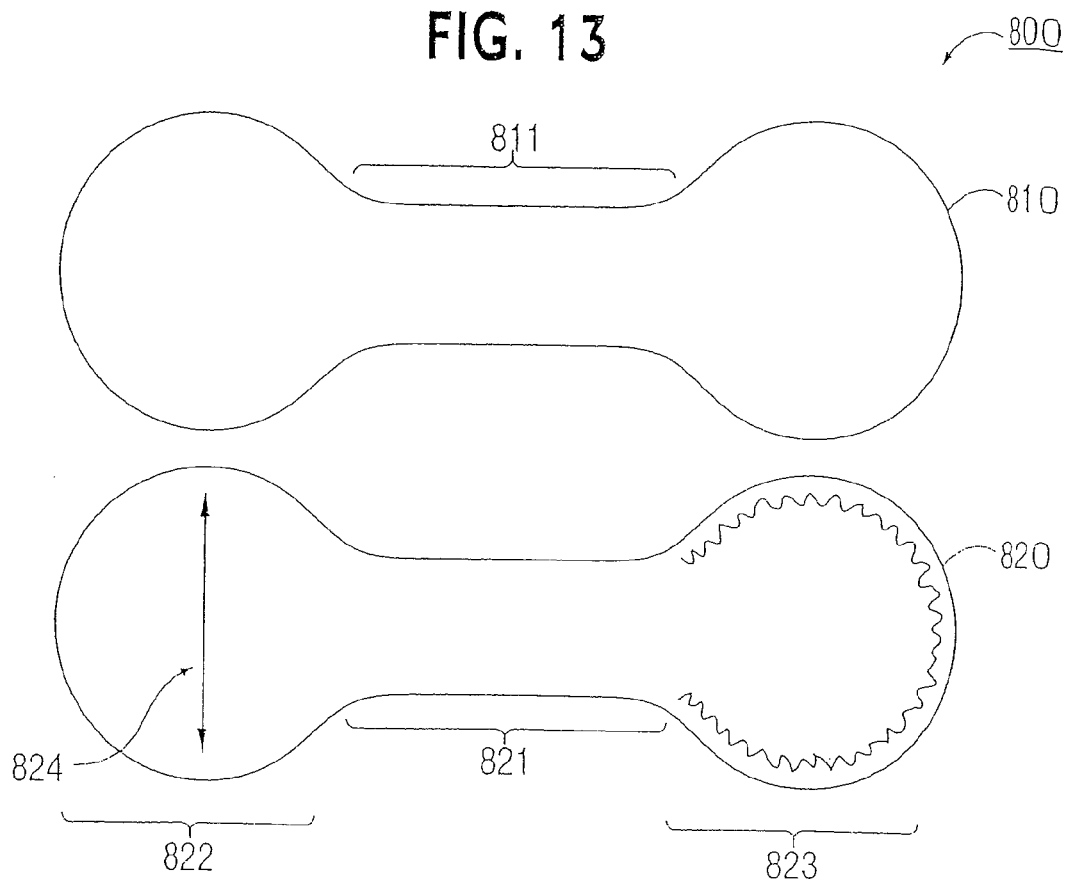
FIG. 13 shows a top view of shell membranes, according another embodiment of the invention.

FIG. 13 shows a top view of shell membranes, according to another embodiment of the invention. As shown in FIG. 13, shell 800 includes an outer membrane 810 and an inner membrane 820. The lengths of band portions 811 and 821 of outer membrane 810 and inner membrane 820, respectively, are greater than the corresponding portion of the frame. This extra length allows the shell 800 to gather with extra material about the portions 811 and 821.

In addition, the ear portions 822 and 823 of inner membrane 820 can have lengths along direction 824 greater than the corresponding ear cup portions of the frame. An elastic membrane, while stretched, can be attached to the perimeter of ear portions 822 and 823. This extra size of ear portions 822 and 823 along direction 824 and the stretched elastic membrane allows the ear portions 822 and 823 to draw inwardly.

Figure 14:
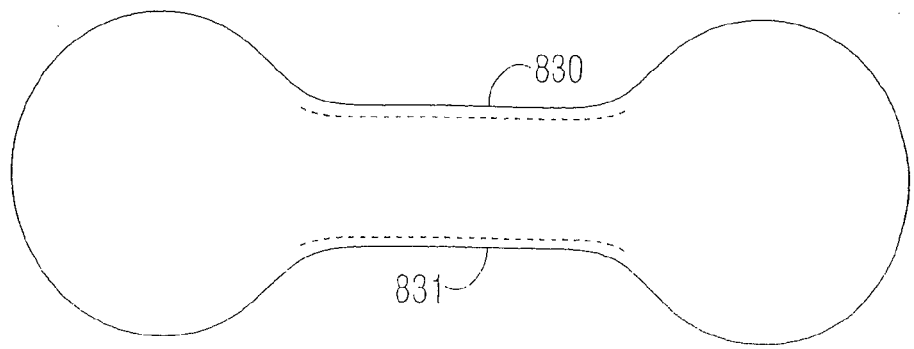
FIG. 14 shows a top view of an assembled shell based on the shell membranes shown in FIG. 13.

FIG. 14 shows a top view of an assembled shell based on the shell membranes shown in FIG. 13. As shown in FIG. 14, the outer membrane 810 and inner membrane 820 can be attached together at the positions 830 and 831. The frame can be inserted into an interior defined between the outer membrane 810 and inner membrane 820. The inward draw of the elastic membrane of ear portions 822 and 823 allows these to gather about the ear cup portions of the frame when inserted into an interior formed by inner membrane 810 and outer membrane 820.

FIG. 15 shows a top view of shell membranes, according to another embodiment of the invention. As shown in FIG. 15, shell 900 includes ear membranes 910, 920, 930 and 940, and middle membrane 950. The middle membrane 950 can be a knit tube or a membrane folded over to form a tube shape. Ear membranes 910 and 930 can be attached together, and ear membranes 920 and 940 can be attached together. Once attached, for example, by sewing, these attached ear membranes can be attached to middle membrane 950. Alternatively, these attached ear membranes can be turned inside out and then attached to middle membrane 950. In yet another alternative, the attached ear membranes can include addition elastic membranes as discussed above in reference to, for example, FIG. 11. FIG. 16 shows a top view of an assembled shell based on the shell membranes shown in FIG. 15.

FIG. 17 shows a perspective view of two band portions, according to an embodiment of the invention. As shown in FIG. 17, band portion 1000 includes a first end 1001, a second end 1002, an inner side 1003 and an outer side 1004. The first end 1001 of band portion 1000 includes an opening. The second end 1002 of band portion 1000 includes a mounting portion 1005. Band portion 1000 has a base member 1006, side members 1007 and upper member 1008. Base member 1006, side members 1007 and upper members 1008 define a passageway along the band portion 1000, lengthwise. The passageway includes openings along the base member 1006, side members 1007 and upper member 1008.

Band portion 1010 includes a first end 1011 and a second end 1012. Band portion 1010 also includes a motion-restraint portion 1013 (shown as a detent in phantom) on the outer side of the first end 1011 of band portion 1010. Band portion 1010 also includes a mounting portion 1015 on the second end 1012.

Band portion 1010 can be slidably engaged into the passageway of band portion 1000. The motion-restraint portion 1013 of band portion 1010 can be engaged through opening 1009 of the passageway. Note that the band portion 1000 can easily flex either inwardly or outwardly because both the base member 1006 and the upper member 1008 have openings. In other words, as the band portions 1000 and 1010 are adjusted (e.g., while band portion 1010 is slidably engaged within the passageway of band portion 1000), these band portions can easily flex inwardly or outwardly due to the openings in the base member 1006 and the upper member 1008 of band portion 1000. In an alternative embodiment, the motion-restraint portion can be integrally formed with the band portion along only a single side of the detent while the remaining sides of the detent are separated (or cut out) from the band portion. Such an embodiment allows the one band portion to be removably and slideably engaged into the passageway of the other band portion.

In another alternative embodiment, the motion-restraint portion can be a disengageable detent. The detent can be removably engageable with any of the openings of the passageway of the other band portion. Thus, the detent can be removably engageable into the openings of the upper member of the other band portion. This allows the band portions to be temporarily locked in multiple possible positions within the range of motion for the one band portion within the passageway of the other band portion. Note also that although the detent can be on the outer side of the band portion thereby corresponding to detent-engageable openings on the upper member of the other band portion, other arrangements are possible. For example, a detent can be located on any of the four sides of the band portion (either alone or in combination with detents on other sides) because the band portion includes openings on its four sides: the base member, the side members and the upper member.

Figure 18:
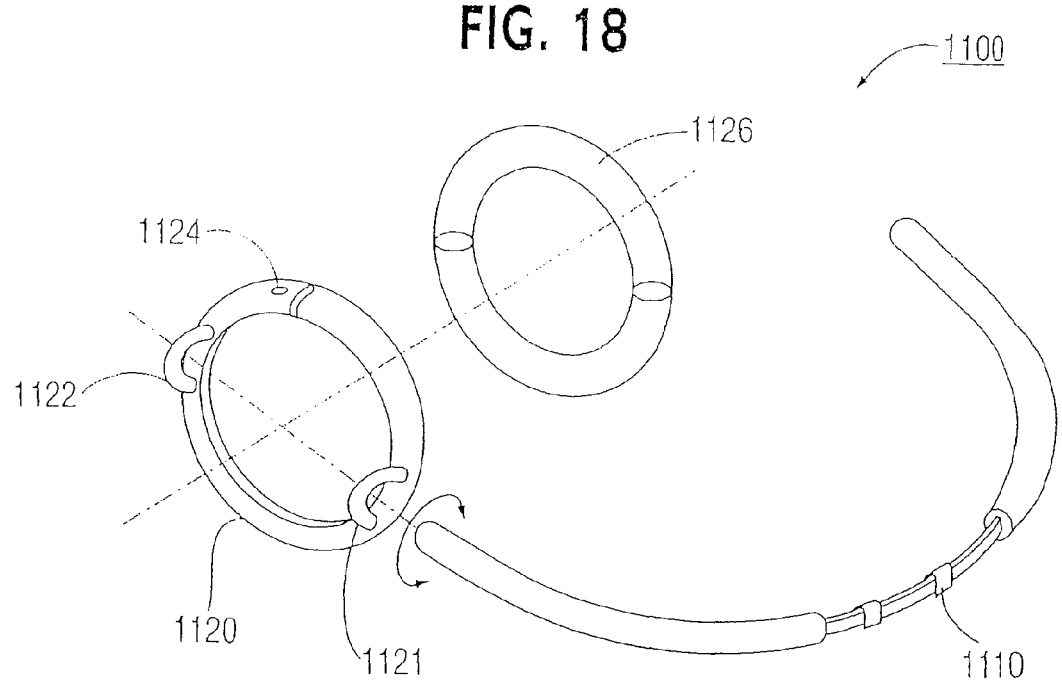
FIG. 18 shows an assembly view of a frame, according another embodiment of the invention.

FIG. 18 shows an assembly view of a frame, according another embodiment of the invention. As shown FIG. 18, the frame 1100 includes a band 1110 and ear cup portion 1120. Note that although a single ear cup portion 1120 is shown in FIG. 18, the frame 1100 includes a second ear cup portion that is attached to the band 1110 on the side opposite from ear cup portion 1120.

Ear cup portion 1120 includes attachment portions 1121 and 1122, ear cup 1124 and cushion insert 1126. Cushion insert 1126 can be made of, for example, urethane foam. The cushion insert 1126 can be attached to ear cup 1124 by, for example, glue. Cushion insert 1126 can provide cushioning between the ear cup 1124 and the user's head.

Attachment portions 1121 and 1122 of ear cup portion 1120 are proximal and distal, respectively, to the band 1110. The end of the band 1110 can be inserted into the attachment portions 1121 and 1122 so that band 1110 is attached to ear cup portion 1120 by, for example, a friction fit. Such a friction fit allows the band 1110 to be removed from and reattached to ear cup portion.

Figure 19:
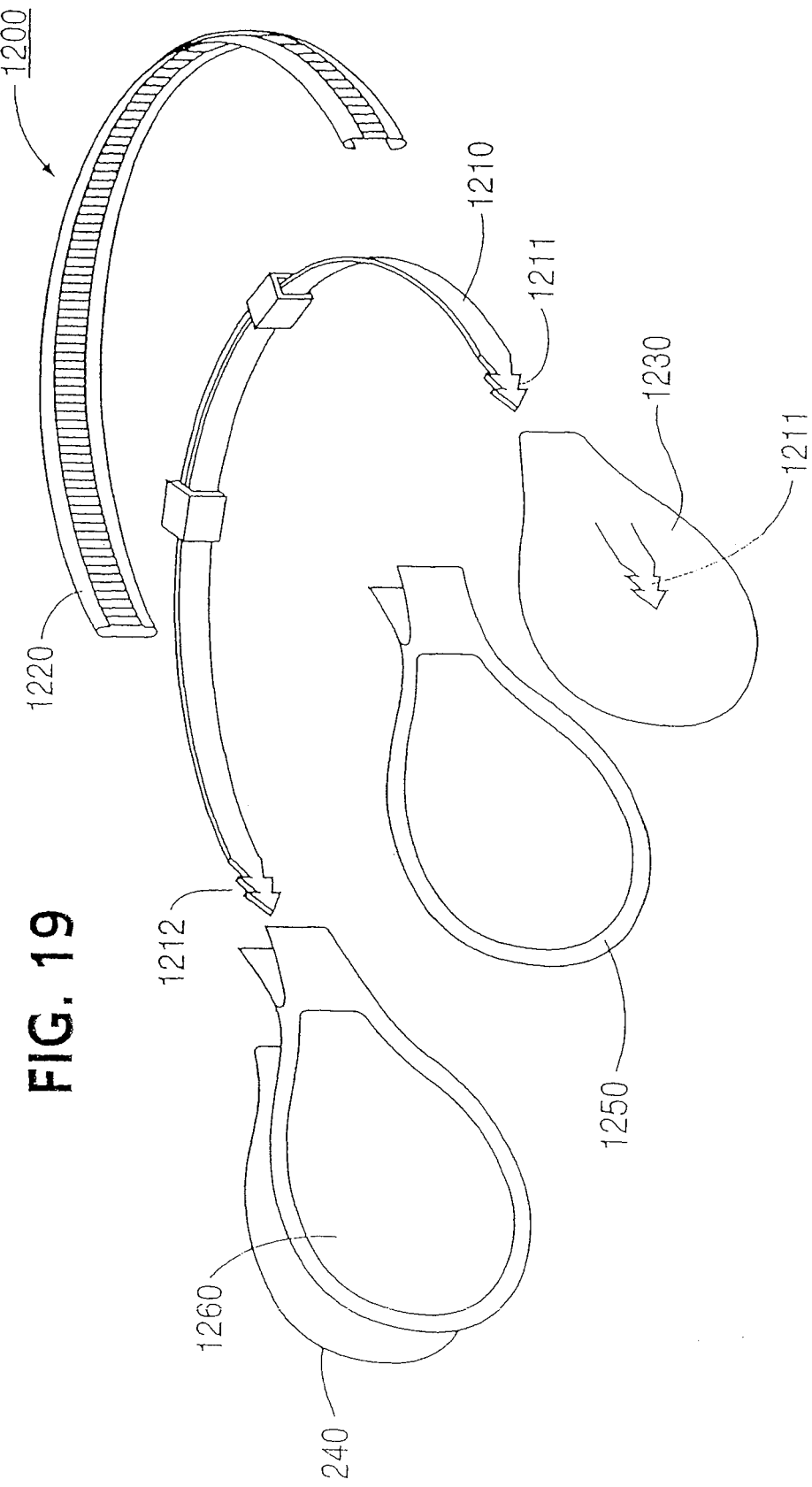
FIG. 19 shows an assembly view of an ear protection device, according to another embodiment of the invention.

FIG. 19 shows an assembly view of an ear protection device, according to another embodiment of the invention. As shown in FIG. 19, ear protection device 1200 includes a band 1210, a band membrane 1220, ear cup portions 1230 and 1240 and ear cup membranes 1250 and 1260. The band membrane 1220 can be, for example, elastic piping with binding on the upper and lower side of the piping that allows the band membrane 1220 to fit over the band 1210. The band 1210 can be, for example, an adjustable spring-like panel having two portions. Each end of the band 1210 can have a protrusion-locking portion 1211 and 1212. More specifically, protrusion-locking portions 1211 and 1212 can have a barbed shape.

Ear cup portions 1230 and 1240 can be made of, for example, a semi-rigid material such as foam. Protrusion-locking portions 1211 and 1212 can be inserted into ear cup portions 1230 and 1240, respectively. Note that protrusion-locking portion 1211 is shown in phantom within ear cup portion 1230 for illustrative purposes. The barbed shape of protrusion-locking portions 1211 and 1212 allows the protrusion-locking portions 1211 and 1212 to be retained within the ear cup portions 1230 and 1240. In one embodiment, protrusion-locking portions 1211 and 1212 can be inserted into ear cup portions 1230 and 1240, respectively, with glue to provide additional retention.

The ear cup membranes 1250 and 1260 each can be made of, for example, a fabric material on both sides thereby forming an interior into which ear cup portions 1230 and 1240, respectively, can be inserted. In other words, ear cup membranes 1250 and 1260 can be covers into which ear cup portions 1230 and 1240, respectively, can be inserted.

Figure 20:
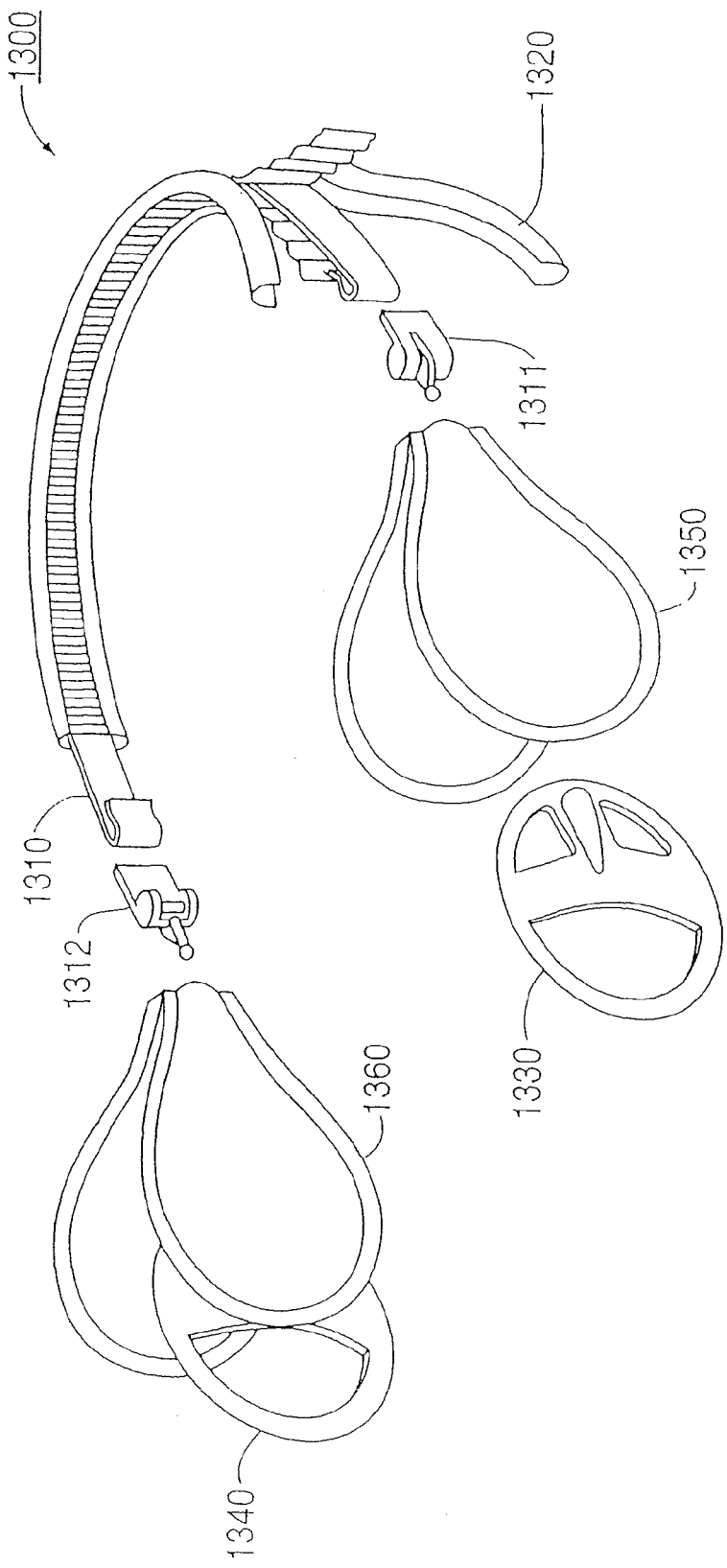
FIG. 20 shows an assembly view of an ear protection device, according to another embodiment of the invention.

FIG. 20 shows an assembly view of an ear protection device, according to another embodiment of the invention. As shown in FIG. 20, ear protection device 1300 includes a band 1310, a band membrane 1320, ear cup portions 1330 and 1340 and ear cup membranes 1350 and 1360. The band membrane 1320 can be, for example, elastic piping with a binding on the upper and lower side of the piping that allows the band membrane 1320 to fit over the band 1310. The band 1310 can be, for example, an adjustable spring-like band having two portions. Each end of the band 1310 can be coupled to a protrusion-locking portion 1311 and 1312. More specifically, protrusion-locking portions 1311 and 1312 can have a ball connector configured to lock into a ball-joint connection with the ear cup portions 1330 and 1340. The protrusion-locking portions 1311 and 1312 can have a post configuration that can friction fit into the clip ends of the band 1310. Such a post-clip configuration allows the ear cup portions 1330 and 1340 to rotate about the ends of band 1310 when in a closed configuration.

Ear cup portions 1330 and 1340 can be made of, for example, molded plastic. Ear cup portions 1330 and 1340 each can include a joint portion of a ball-joint connection that is configured to connect with protrusion-locking portions 1311 and 1312. The joint portion of each ear cup portions 1330 and 1340 can be disposed at an end proximal to protrusion-locking portions 1311 and 1312. Thus, protrusion-locking portions 1311 and 1312 can be removably connected to ear cup portions 1330 and 1340, respectively.

The ear cup membranes 1350 and 1360 each can be made of, for example, a fabric material on both sides thereby forming an interior into which ear cup portions 1330 and 1340, respectively, can be inserted. In other words, ear cup membranes 1350 and 1360 can be covers into which ear cup portions 1330 and 1340, respectively, can be inserted.

Figure 21:
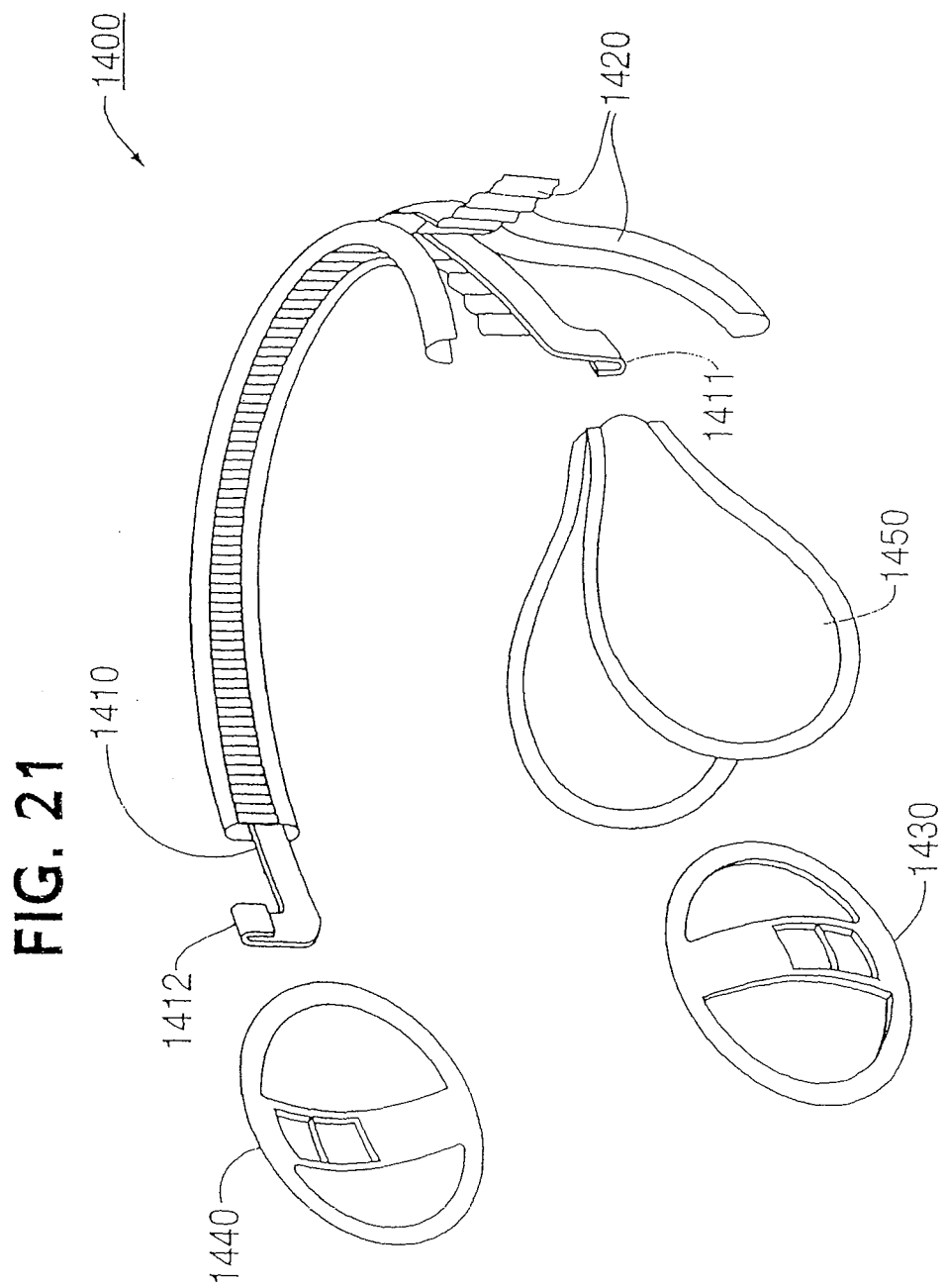
FIG. 21 shows an assembly view of an ear protection device, according to another embodiment of the invention.

FIG. 21 shows an assembly view of an ear protection device, according to another embodiment of the invention. As shown in FIG. 21, ear protection device 1400 includes a band 1410, a band membrane 1420, ear cup portions 1430 and 1440 and ear cup membrane 1450. The band membrane 1420 can be, for example, elastic piping with a binding on the upper and lower side of the piping that allows the band membrane 1420 to fit over the band 1410. The band 1410 can be, for example, an adjustable spring-like band having two portions. Each end of the band 1410 can be coupled to a protrusion-locking portion 1411 and 1412. More specifically, protrusion-locking portions 1411 and 1412 each can have a clamp connector configured to lock by a friction fit into a post within the ear cup portions 1430 and 1440. Such a hinge-post configuration allows the ear cup portions 1430 and 1440 to rotate about the ends of band 1410 when in a closed configuration.

Ear cup portions 1430 and 1440 can be made of, for example, molded plastic. Protrusion-locking portions 1411 and 1412 can be removably connected to ear cup portions 1430 and 1440, respectively.

The ear cup membrane 1450 can be made of, for example, a fabric material on both sides thereby forming an interior into which ear cup portion 1430 can be inserted. In other words, ear cup membrane 1450 can be a cover into which ear cup portion 1430 can be inserted. Note that although not shown in FIG. 21, an additional ear cup membrane can be used to cover ear cup portion 1440.

Figure 22:
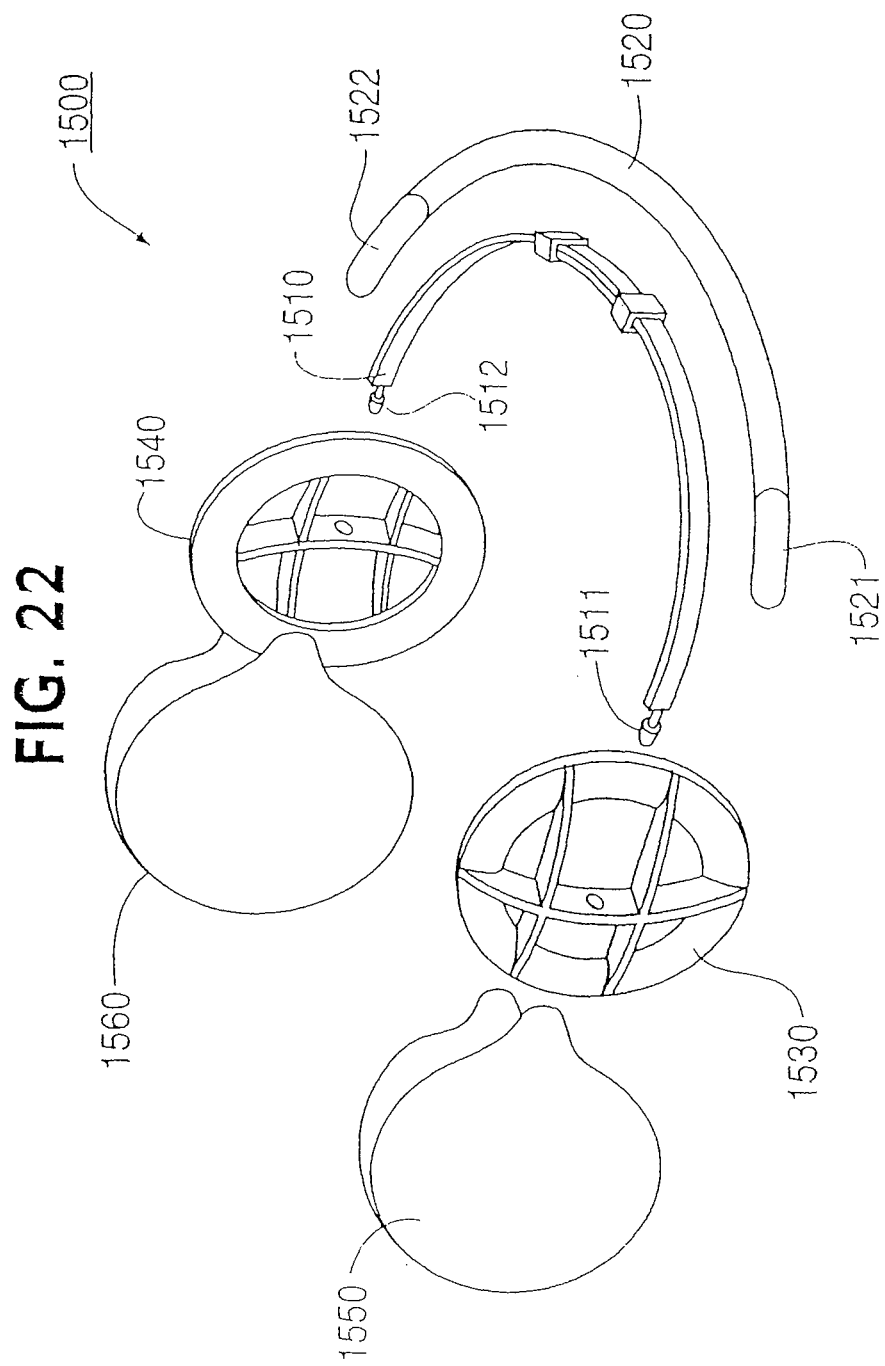
FIG. 22 shows an assembly view of an ear protection device, according to another embodiment of the invention.

FIG. 22 shows an assembly view of an ear protection device, according to another embodiment of the invention. As shown in FIG. 22, ear protection device 1500 includes a band 1510, a band membrane 1520, ear cup portions 1530 and 1540 and ear cup membranes 1550 and 1560. The band membrane 1520 can be, for example, a cloth tube into which band 1510 can be inserted. The band membrane 1520 can include ends 1521 and 1522 that can be made of, for example, lycra or similar elastic material. The band 1510 can be, for example, an adjustable spring-like band having two portions. One end of the band 1510 includes a protrusion-locking portion 1511 and the other end of band 1510 includes a protrusion-locking portion 1512. More specifically, protrusion-locking portions 1511 and 1512 each can have a knob configured to lock by a snap fit into a hole in the ear cup portions 1530 and 1540. Such a snap-fit configuration allows the ear cup portions 1530 and 1540 to rotate about the ends of band 1510 when in a closed configuration.

Ear cup portions 1530 and 1540 can be made of, for example, molded plastic. The ear cup membranes 1550 and 1560 each can be made of, for example, a fabric material on both sides thereby forming an interior into which ear cup portions 1530 and 1540 can be inserted. In other words, ear cup membranes 1550 and 1560 can be a cover into which ear cup portions 1530 and 1540 can be inserted.

While various embodiments of the invention have been described above, it should be understood that they have been presented by way of example only, and not limitation. Thus, the breadth and scope of the present invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

For example, although certain frame embodiments are described as being inserted into certain shell embodiments, other arrangements are possible. Any of the frame embodiments described above can be inserted into other shell configurations disclosed in, for example, U.S. Pat. No. 5,835,609, and U.S. application Ser. Nos. 09/521,241 and 09/978, 591, now U.S. Pat. Nos. 6,332,223 and 6,502,247 respectively, both of which are entitled "Apparatus and Method for Making an Ear Warmer Having Interior Seams." In addition, any of the shell embodiments described above can be used in combination with the frames described in U.S. Pat. No. 5,835,609. The entire disclosures of U.S. Pat. No. 5,835,609 and U.S. application Ser. Nos. 09/521,241 and 09/978,591, now U.S. Pat. Nos. 6,332,223 and 6,502,247 respectively, are incorporated herein by reference.

What is claimed is:

1. An apparatus, comprising:
   an outer membrane including a first ear portion and a second ear portion,
   a first piece of elastic material coupled to a first end portion of the outer membrane, the first end portion of the outer membrane including a portion of a perimeter of the first ear portion of the outer membrane and excluding a center of the first ear portion of the outer membrane, the first piece of elastic material having a length and a width shorter than the length, the first piece of elastic material not directly coupled to the center of the first ear portion of the outer membrane;
   a second piece of elastic material coupled to a second end portion of the outer membrane;
   an inner membrane including a first ear portion and a second ear portion, the inner membrane coupled to the outer membrane;
   a third piece of elastic material coupled to a first end portion of the inner membrane; and
   a fourth piece of elastic material coupled to a second end portion of the inner membrane.

2. The apparatus of claim 1, wherein:
   the outer membrane includes a middle portion located between the first ear portion of the outer membrane and the second ear portion of the outer membrane, and
   the inner membrane includes a middle portion located between the first ear portion of the inner membrane and the second ear portion of the inner membrane.

3. The apparatus of claim 2, wherein the first ear portion of the outer membrane is disposed between the first end portion of the outer membrane and the middle portion of the outer membrane, and the second ear portion of the outer membrane is disposed between the second end portion of the outer membrane and the middle portion of the outer membrane.

4. The apparatus of claim 2, wherein a first perimeter portion of the outer membrane is sewn to a perimeter portion of the inner membrane, a second perimeter portion of the outer membrane is not sewn to the inner membrane, the second perimeter portion of the outer membrane including the first end portion of the outer membrane.

5. The apparatus of claim 1, wherein the first piece of elastic material is configured to apply a force to cause at least a portion of the outer membrane to conform to an ear member of a frame disposed between the inner member and the outer member.

6. The apparatus of claim 1, wherein the first piece of elastic material is configured to cause the outer membrane to form gathers when the first piece of elastic material is in a relaxed configuration.

7. The apparatus of claim 1, wherein:
   the first end portion of the inner membrane is along a perimeter of the first ear portion of the inner membrane; and
   the second end portion of the outer membrane is along a perimeter of the second ear portion of the outer membrane.

8. The apparatus of claim 1, wherein each of the second piece of elastic material, the third piece of elastic material, and the fourth piece of elastic material have a length and a width shorter than the length.

9. An apparatus, comprising:
   an ear warmer shell having a first membrane, a second membrane, and an elastic membrane,
   the first membrane having a first ear portion, a second ear portion, and a middle portion,
   at least a portion of the second membrane coupled to the first membrane,
   the elastic membrane disposed between the second membrane and the first ear portion of the first membrane, the elastic membrane not disposed between the second membrane and the middle portion of the first membrane,
   the first ear portion of the first membrane includes a central portion, the elastic membrane not disposed between the second membrane and the central portion of the first membrane; and
   a frame, at least a portion of the frame configured to be disposed within the ear warmer shell via an opening defined, at least in part, by a portion of the first membrane and a portion of the second membrane, when the ear warmer shell is fully assembled the elastic membrane configured to be disposed around a perimeter portion of the frame when the frame is disposed within the ear warmer shell.

10. The apparatus of claim 9, wherein the elastic membrane is a first elastic membrane, the first elastic membrane is coupled to the first membrane, the apparatus further comprising:
    a second elastic membrane coupled to the second membrane.

11. The apparatus of claim 9, wherein the portion of the first membrane and the portion of the second membrane define, at least in part, the opening such that the opening is configured to receive an ear portion of the frame, the elastic membrane is configured to apply a force to secure the apparatus to the frame.

12. The apparatus of claim 9, wherein the first membrane and the second membrane collectively define an outer perimeter, the portion of the second membrane coupled to the first membrane along the outer perimeter to define an attachment portion, the attachment portion being entirely disposed within an interior region defined by the first membrane and the second membrane.

13. The apparatus of claim 9, wherein the elastic membrane is coupled to at least a portion of a perimeter portion of the first membrane, the elastic membrane configured to apply a force to cause at least a portion of the first membrane to conform to an ear portion of the frame.

14. The apparatus of claim 9, wherein a first perimeter portion of the middle portion is configured to be coupled to a second perimeter portion of the middle portion defining a pocket, the pocket configured to receive at least a portion of the frame.

15. The apparatus of claim 9, wherein the elastic membrane is configured to cause the first membrane to form gathers when the elastic membrane is in a relaxed configuration.

16. The apparatus of claim 9, wherein a first perimeter portion of the first membrane is coupled to the second membrane, the first perimeter portion of the first membrane is mutually exclusive from a second perimeter portion of the first membrane, the second perimeter portion of the first membrane defining, at least in part, the opening.

17. The apparatus of claim 9, wherein the first membrane is physically distinct from the second membrane.

18. The apparatus of claim 9, wherein the at least the portion of the frame is configured to be removeably inserted into the ear warmer shell via the opening.

19. An apparatus, comprising:
- an ear warmer shell including a first membrane and a second membrane, the second membrane being physically distinct from the first membrane, the first membrane having a first ear portion, a second ear portion, and a middle portion;
- an elastic membrane disposed between the second membrane and the first ear portion of the first membrane, the elastic membrane not disposed between the second membrane and the middle portion of the first membrane, the elastic membrane has a length and a width shorter than the length, the elastic membrane disposed along a perimeter portion of the first ear portion of the first membrane; and
- a frame configured to be disposed between the first membrane and the second membrane via an opening defined by the ear warmer shell.

20. The apparatus of claim 19, wherein the opening is defined by the ear warmer shell when the ear warmer shell is fully assembled.

* * * * *